US010790068B2

(12) United States Patent
Milstein et al.

(10) Patent No.: US 10,790,068 B2
(45) Date of Patent: *Sep. 29, 2020

(54) DEVICE AND METHOD FOR PROTECTION FROM RADIATION IN SPACE

(71) Applicant: StemRad Ltd., Tel Aviv (IL)

(72) Inventors: Oren Milstein, Tel Aviv (IL); Gideon Waterman, Tel Aviv (IL); Meytal Baron, Tel Aviv (IL); Ethan Shiloh, Tel Aviv (IL); Jonathan Roth, Karkur (IL); Tamar Nix, Haifa (IL)

(73) Assignee: STEMRAD LTD., Tel Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/392,071

(22) Filed: Apr. 23, 2019

(65) Prior Publication Data

US 2019/0252087 A1    Aug. 15, 2019

Related U.S. Application Data

(63) Continuation of application No. 15/558,203, filed as application No. PCT/IL2016/050298 on Mar. 17, 2016, now Pat. No. 10,276,273.

(60) Provisional application No. 62/239,886, filed on Oct. 10, 2015, provisional application No. 62/134,274, filed on Mar. 17, 2015.

(51) Int. Cl.
*G21F 3/025* (2006.01)
*G21F 1/02* (2006.01)
*A61B 6/10* (2006.01)

(52) U.S. Cl.
CPC .............. *G21F 3/025* (2013.01); *A61B 6/107* (2013.01); *G21F 1/02* (2013.01)

(58) Field of Classification Search
CPC .................... G21F 3/025; A41D 31/0094
USPC ................. 250/505.1, 515.1, 516.1
See application file for complete search history.

(56) References Cited

U.S. PATENT DOCUMENTS

| 3,233,248 A | 2/1966 | Bushnell |
| 3,310,053 A | 3/1967 | Greenwood |
| 3,463,150 A | 8/1969 | Penfold |
| 3,465,153 A | 9/1969 | Libby |

(Continued)

FOREIGN PATENT DOCUMENTS

| CN | 2678066 Y | 2/2005 |
| DE | 1918244 U | 6/1965 |

(Continued)

OTHER PUBLICATIONS

Baiocco, G. et al., "A Water-Filled Garment to Protect Astronauts During Interplanetary Missions Tested on Board the ISS" Life Sciences in Space Research (2018) vol. 18, pp. 1-11.

(Continued)

*Primary Examiner* — Nicole M Ippolito
*Assistant Examiner* — Hanway Chang
(74) *Attorney, Agent, or Firm* — Troutman Pepper Hamilton Sanders LLP

(57) ABSTRACT

A device for protection of a body from radiation includes at least one flexible garment. Each section of the flexible garment is configured to shield a region of a surface of the body. Each section complementarily attenuates self-shielding by internal structure between the region and an interior region of the body such that radiation at the interior region is attenuated to a predefined attenuation level.

16 Claims, 9 Drawing Sheets

(56) References Cited

U.S. PATENT DOCUMENTS

| | | | |
|---|---|---|---|
| 3,996,620 | A | 12/1976 | Maine |
| 4,196,355 | A | 4/1980 | Maine |
| 4,386,277 | A | 5/1983 | Forshee |
| 5,028,796 | A | 7/1991 | Swartz |
| 5,103,504 | A | 4/1992 | Dordevic |
| 5,621,188 | A | 4/1997 | Lee et al. |
| 5,745,925 | A | 5/1998 | Ghilardi et al. |
| 6,101,711 | A | 8/2000 | Kobayashi |
| 6,531,086 | B1 | 3/2003 | Larsson |
| 6,841,791 | B2 | 1/2005 | DeMeo et al. |
| 8,586,090 | B2 | 11/2013 | Dadachova et al. |
| 10,276,273 | B2* | 4/2019 | Milstein .................. G21F 3/025 |
| 2005/0211930 | A1 | 9/2005 | DeMeo et al. |
| 2006/0108548 | A1 | 5/2006 | Cadwalader et al. |
| 2007/0132943 | A1 | 6/2007 | Kurzrok |
| 2007/0237829 | A1 | 10/2007 | Dadachova et al. |
| 2008/0272318 | A1 | 11/2008 | Cadwalader et al. |
| 2009/0000007 | A1 | 1/2009 | DeMeo |
| 2009/0156982 | A1 | 6/2009 | Petrie et al. |
| 2013/0112924 | A1 | 5/2013 | Eckhoff et al. |
| 2013/0240763 | A1 | 9/2013 | Khandkar et al. |
| 2014/0021377 | A1 | 1/2014 | Khandkar et al. |
| 2014/0151584 | A1 | 6/2014 | Khandkar et al. |
| 2016/0324490 | A1 | 11/2016 | Brachman et al. |
| 2017/0119106 | A1 | 5/2017 | Leslie |

FOREIGN PATENT DOCUMENTS

| | | |
|---|---|---|
| DE | 1918244 A1 | 11/1970 |
| DE | 4132925 A1 | 4/1993 |
| EA | 003918 B1 | 10/2003 |
| EP | 0173757 A1 | 3/1986 |
| EP | 1052652 A2 | 11/2000 |
| JP | 2002091599 A | 3/1990 |
| JP | H02501769 A | 6/1990 |
| JP | H02124600 U | 10/1990 |
| JP | 2001242288 A | 9/2001 |
| JP | 2002131475 A | 5/2002 |
| JP | 2002267793 A | 9/2002 |
| JP | 2005538356 A | 12/2005 |
| JP | 2010133772 A | 6/2010 |
| JP | 201376693 A | 4/2013 |
| JP | 5532463 B2 | 5/2014 |
| KR | 1020010095618 A | 11/2011 |
| WO | 2012154962 A2 | 11/2012 |
| WO | 2014163574 A1 | 10/2014 |
| WO | 2016147193 A1 | 9/2016 |

OTHER PUBLICATIONS

Baiocco, G. et al., "PERSEO: PErsonal Radiation Shielding for intErplanetary MissiOns: Executive Summary" ESA (2015) 4 pages total.

Vuolo, M. et al., "Exploring Innovative Radiation Shielding Approaches in Space: A Material and Design Study for a Wearable Radiation Protection Spacesuit" Life Sciences in Space Research (2017) vol. 15, pp. 69-78.

Vuolo, M. et al., "PERSEO: PErsonal Radiation Shielding for intErplanetary MissiOns: Final Report" ESA (2015) pp. 1-66.

Communication (Chinese First Office Action) issued by the State Intellectual Property Office of the People's Republic of China in Chinese Patent Application No. 201280034481.7, dated May 5, 2015, 16 pages total.

Communication (Chinese Fourth Office Action) issued by the State Intellectual Property Office of the People's Republic of China in Chinese Patent Application No. 201280034481.7, dated Apr. 6, 2017, 8 pages total.

Communication (Chinese Second Office Action) issued by the State Intellectual Property Office of the People's Republic of China in Chinese Patent Application No. 201280034481.7, dated Mar. 11, 2016, 8 pages total.

Communication (Chinese Third Office Action) issued by the State Intellectual Property Office of the People's Republic of China in Chinese Patent Application No. 201280034481.7, dated Oct. 8, 2016, 8 pages total.

Communication issued by Canada Patent Application by the Canadian Intellectual Property Office in Canadian Patent Application No. 2,835,601, dated May 14, 2018, 5 pages total.

Dillard, M.A., "Radiation Shielding Garment Technologies" (2015) accessed from: https://www.nasa.gov/sites/default/files/atoms/files/radiationshieldinggarmenttechnologies.docx, 2 pages total.

European Communication (Extended European Search Report) for European Application No. EP 16764351.9, dated Oct. 9, 2018, 10 pages total.

European Communication (Extended European Search Report) for European Application No. EP 18187144.3, dated Dec. 20, 2018, 11 pages total.

Communication (pursuant to Article 94(3) EPC) issued by the European Patent Office in European Patent Application No. 12782620.4, dated Nov. 17, 2015, 7 pages total.

Communication (Extended European Search Report) issued by the European Patent Office in European Patent Application No. 12782620.4, dated Sep. 12, 2014, 8 pages total.

International Preliminary Report of Patentability of the International Searching Authority for International Application No. PCT/US2012/037335, dated Nov. 12, 2013, 7 pages total.

International Preliminary Report on Patentability for PCT Application No. PCT/IL2016/050298 dated Sep. 19, 2017, 9 pages total.

International Search Report and Written Opinion for PCT Application No. PCT/IL2016/050298 dated Jul. 11, 2016, 16 pages total.

International Search Report of Application No. PCT/US2012/037335, dated Nov. 28, 2012, 4 pages total.

Communication (Decision of Refusal) issued by the Japan Patent Office in Japanese Patent Application No. 2014-510468, dated Feb. 7, 2017, 13 pages total.

Communication (Notification of Reasons for Refusal) issued by the Japan Patent Office in Japanese Patent Application No. 2014-510468, dated Mar. 22, 2016, 8 pages total.

Office Action for EA Application No. 201391671, dated Nov. 2, 2016, 4 pages total.

Iscove, N.N. et al., "Colony Formation by Normal and Leukemic Human Marrow Cells in Culture: Effect of Conditioned Medium From Human Leukocytes" Blood: The Journal of Hematology (1971) vol. XXXVII, No. 1, pp. 1-5.

Ware, J. et al., "Design and Testing of Improved Spacesuit Shielding Components" Lawrence Berkeley National Laboratory (2002).

Wilson, J.W. et al., "Spacesuit Radiation Shield Design Methods" (1997) accessed from: https://ntrs.nasa.gov/archive/nasa/casi.ntrs.nasa.gov/20060046504.pdf, 16 pages total.

Written Opinion for PCT Application No. PCT/IL2016/050298 dated Jul. 11, 2016, 8 pages total.

Written Opinion of the International Searching Authority for International Application No. PCT/US2012/037335, dated Nov. 28, 2012, 6 pages total.

\* cited by examiner

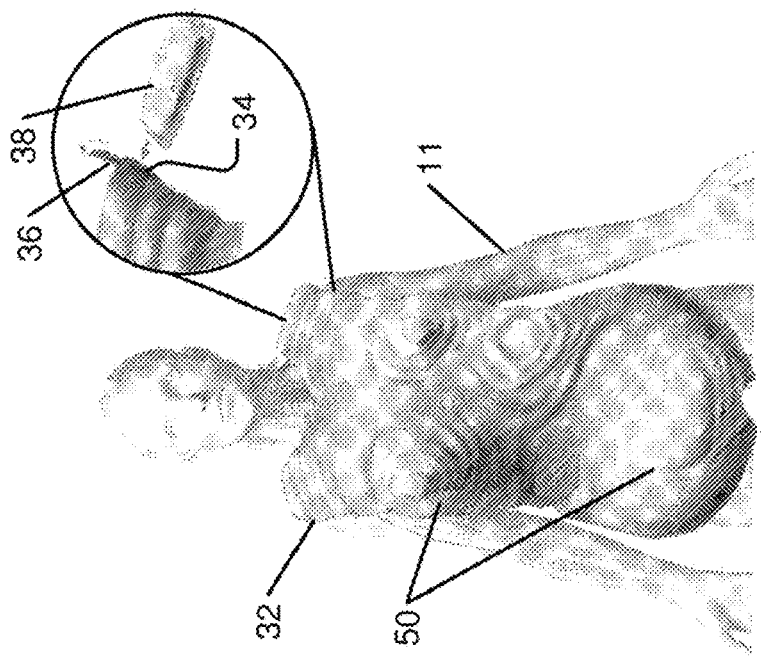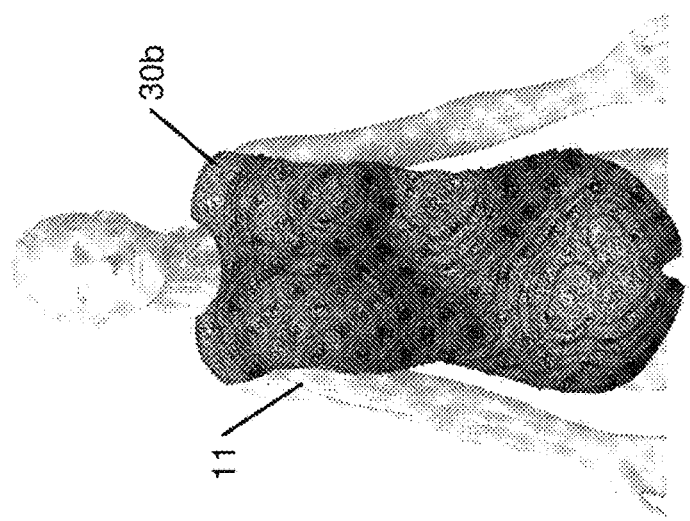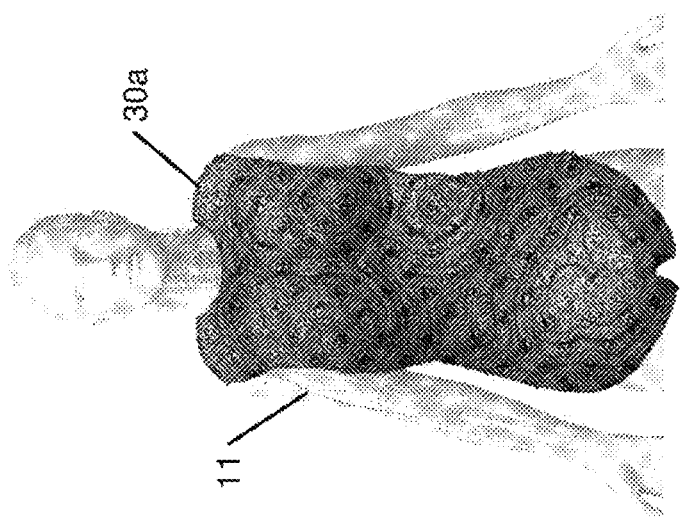

DEVICE AND METHOD FOR PROTECTION FROM RADIATION IN SPACE

CROSS-REFERENCE TO RELATED APPLICATIONS

This application is a Continuation of U.S. application Ser. No. 15/558,203, filed on Sep. 14, 2017, which is a U.S. National Stage of International Application No. PCT/IL2016/050298 filed Mar. 17, 2016, which claims priority to U.S. Provisional Application Nos. 62/134,274, filed Mar. 17, 2015, and 62/239,886 filed Oct. 10, 2015. All above applications are incorporated herein by reference in their entireties.

FIELD OF THE INVENTION

The present invention relates to protection against ionizing radiation. More particularly the present invention relates to a radiation protection device and method for use in space.

BACKGROUND OF THE INVENTION

On space missions beyond low Earth orbit, such as on missions to Earth's moon, to Mars, or elsewhere, Earth's atmosphere and magnetosphere are not available to protect the crew of the mission from sources of ionizing radiation. Such radiation may include the solar wind, cosmic radiation, solar flares or other solar particle events, and other radiation sources or events. Effects of exposure to radiation from a major solar event or other radiation event could place the crew of a space mission at significant risk for acute radiation sickness. Such acute exposure could impact crew health and performance during their mission, endangering completion of the mission and the safe return of the crew to Earth. Protracted exposure to lower levels of radiation (e.g., the solar wind or cosmic radiation) may increase the likelihood of cancer or other radiation-induced disorders for crew members many years after the completion of their mission.

Shielding the entire habitable area or cabin of a spacecraft is not currently feasible. Effectively shielding an entire crew module (such as that of the Orion spacecraft) would require very large quantities of shielding material. Delivering such a quantity of shielding material to space would entail much added expense and time, or would require use of a lunch vehicle that is larger than any that are expected to be available in the foreseeable future. Addition of the extra mass without a corresponding increase in propulsion power could increase travel time to a destination, increasing exposure to the radiation. In addition, such cabin shielding would not provide any shielding for an astronaut during and extravehicular activities.

Drugs are under development to mimic or enhance the body's natural capacity to repair damage caused by radiation. Although there has been some progress in development of drugs for countering the effects of terrestrial ionizing radiation, such as gamma radiation, very little progress has been made towards countering the effects of the type of radiation (high-energy and massive charged particles) that is encountered during space travel. If such a drug were to be developed, it would probably have to be administered several hours before exposure. However, solar particle events cannot currently be forecast in advance. Furthermore, pharmaceuticals have been found to become unstable during space travel, possibly due to protracted exposure to radiation and vibration.

Magnetic deflection and electrostatic repulsion has been considered for reducing exposure to radiation in space. However, a compact system may require magnetic field strength as large as 10 tesla to 20 tesla. Such high fields have been known to produce headaches and migraines in magnetic resonance imaging patients, and long-duration exposure to such fields has not been studied. Devices to produce such a magnetic field may add thousands of kilograms to the mass of the spacecraft.

Personal shielding that is worn on an astronaut's or other user's body enables placement of the shielding adjacent to the area of coverage. The solid angle of coverage is thus maximized, thus enabling a reduction (relative to shielding of an entire cabin or spacecraft) in the mass of shielding that is required to provide equivalent protection.

SUMMARY OF THE INVENTION

There is thus provided, in accordance with an embodiment of the present invention, a device for protection of a body from radiation, the device including at least one flexible garment, each section of the at least one flexible garment being configured to shield a region of a surface of the body such that the each section complementarily attenuates self-shielding by internal structure between the region and an interior region of the body such that radiation at the interior region is attenuated to a predefined attenuation level.

Furthermore, in accordance with an embodiment of the present invention, a garment of the at least one flexible garment includes a plurality of shield elements incorporated into the flexible substrate.

Furthermore, in accordance with an embodiment of the present invention, the flexible substrate or the plurality of shield elements includes a polymer.

Furthermore, in accordance with an embodiment of the present invention, the plurality of shield elements is embedded within the flexible substrate.

Furthermore, in accordance with an embodiment of the present invention, each of the plurality of shield elements has an inward facing surface that is greater than an opposite outward facing surface, such that tapering gaps are formed in between adjacent shield elements of the plurality of shield elements.

Furthermore, in accordance with an embodiment of the present invention, the substrate fully or partially fills the gaps.

Furthermore, in accordance with an embodiment of the present invention, the flexible substrate includes a foam.

Furthermore, in accordance with an embodiment of the present invention, the plurality of shield elements includes a plurality of sequins that are attached to the flexible substrate and wherein the flexible surface includes a fabric sheet.

Furthermore, in accordance with an embodiment of the present invention, the fabric sheet forms a webbing between the plurality of sequins.

Furthermore, in accordance with an embodiment of the present invention, a garment of the at least one garment includes a plurality of the fabric sheets formed into layers.

Furthermore, in accordance with an embodiment of the present invention, a sequin of the plurality of sequins on one fabric sheet of the plurality of the fabric sheets is positioned to overlie a gap between adjacent sequins of the plurality of sequins on another fabric sheet of the plurality of fabric sheets.

Furthermore, in accordance with an embodiment of the present invention, the plurality of shield elements includes a plurality of bags, each of the bags being configured to be filled with a liquid.

Furthermore, in accordance with an embodiment of the present invention, the flexible substrate includes a plurality of flexible bag holders, each of the plurality of bags being configured to be inserted into a bag holder of the plurality of flexible bag holders.

Furthermore, in accordance with an embodiment of the present invention, a shield element of the plurality of shield elements includes a plurality of stacked liquid-fillable compartments.

Furthermore, in accordance with an embodiment of the present invention, the device includes a tube to enable introduction of a liquid into a liquid-fillable compartment of the plurality of stacked liquid-fillable compartments or removal of the liquid from a liquid-fillable compartment of the plurality of stacked liquid-fillable compartments Furthermore, in accordance with an embodiment of the present invention, the at least one garment includes a plurality of garments that are configured to be worn in layers, wherein one garment of the plurality of garments is configured such that a shield element of the plurality of shield elements on the one garment is configured to overlie a gap between two adjacent shield elements on another garment of the plurality of garments.

Furthermore, in accordance with an embodiment of the present invention, the interior region includes tissue-resident stem cells.

Furthermore, in accordance with an embodiment of the present invention, the tissue-resident stem cells are selected from a group of tissue-resident stem cells consisting of distal airway stem cells of the lung, CD34+ hematopoietic stem cells, and intestinal LGR5+ stem cells.

There is further provided, in accordance with an embodiment of the present invention, a method for preventing a radiation-induced condition in a body in space, the method including: determining a required attenuation of radiation at an interior region of the body so as to prevent the radiation-induced condition under an anticipated exposure of the body to radiation; determining self-shielding from the radiation corresponding to each surface region of a plurality of regions of a surface of the body by determining attenuation of the radiation by internal structure of the body that lies between the interior region and the each surface region; and providing a radiation protection device including at least one flexible garment, each section of the at least one flexible garment being configured to attenuate radiation to a shielded surface region of plurality of regions of a surface of the body to complementarily attenuate the self-shielding by the shielded surface region.

Furthermore, in accordance with an embodiment of the present invention, the radiation-induced condition includes mutagenesis or destruction of stem cells and the interior region includes a stem cell niche.

Furthermore, in accordance with an embodiment of the present invention, determining the required radiation attenuation includes determining an attenuation required to prevent a Bragg peak of the radiation from occurring within the interior region.

Furthermore, in accordance with an embodiment of the present invention, determining the required attenuation of radiation includes determining total areal density of shielding to the interior region to prevent the radiation-induced condition, the determined self-shielding includes an areal density of the internal structure that lies between the interior region and the each surface region, and wherein an areal density of the each section is at least a difference between the total areal density and the areal density of the internal structure.

BRIEF DESCRIPTION OF THE DRAWINGS

In order for the present invention, to be better understood and for its practical applications to be appreciated, the following Figures are provided and referenced hereafter. It should be noted that the Figures are given as examples only and in no way limit the scope of the invention. Like components are denoted by like reference numerals.

FIG. 5A schematically illustrates an inner garment layer of a radiation protection device, the garment layer having shield elements in the form of sequins, in accordance with an embodiment of the present invention.

FIG. 5B schematically illustrates a middle garment layer with shield elements in the form of sequins and worn over the inner garment layer shown in FIG. 5A.

FIG. 5C schematically illustrates an outer garment layer with liquid shield elements worn over the garment layers shown in FIG. 5B.

DETAILED DESCRIPTION OF THE INVENTION

Figure 1:
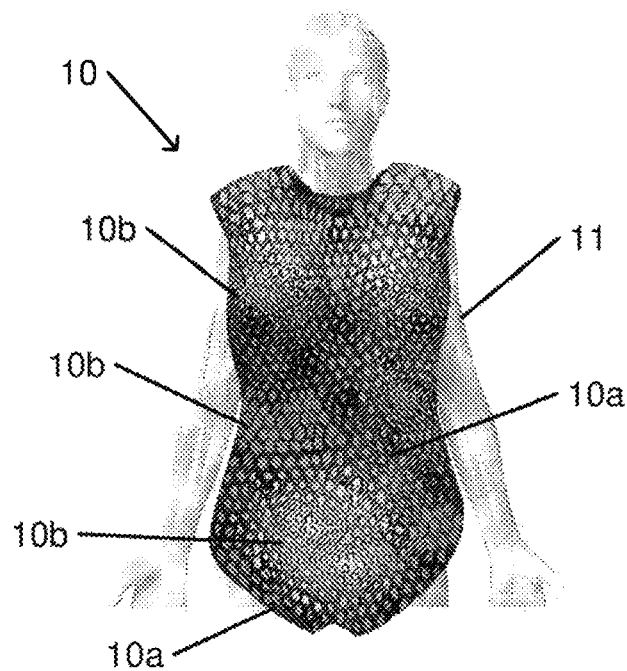
FIG. 1 schematically illustrates a radiation protection device, in accordance with an embodiment of the present invention.

In the following detailed description, numerous specific details are set forth in order to provide a thorough understanding of the invention. However, it will be understood by those of ordinary skill in the art that the invention may be practiced without these specific details. In other instances, well-known methods, procedures, components, modules, units and/or circuits have not been described in detail so as not to obscure the invention.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium (e.g., a memory) that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method embodiments described herein are not constrained to a particular order or sequence.

Additionally, some of the described method embodiments or elements thereof can occur or be performed simultaneously, at the same point in time, or concurrently. Unless otherwise indicated, the conjunction "or" as used herein is to be understood as inclusive (any or all of the stated options).

In accordance with an embodiment of the present invention, a personal radiation protection device is configured to differentially shield different regions of a body from one or more types of space radiation. The radiation protection device is in the form of one or more garments that may be worn over the body. As used herein, a body refers to a body of a living human or animal (although for research, evaluation, or testing purposes, the garment may be used to shield a cadaver, phantom, or other inanimate object).

As used herein, space radiation refers to radiation that is primarily in the form of energetic massive particles (e.g., baryonic particles, such as protons, neutron, light or heavy nuclei, or other baryons, or mesons). Typical sources of space radiation may include solar flares or other solar particle events, galactic cosmic radiation, the solar wind, or other sources of energetic baryons or mesons. In some cases, interaction of the space radiation with matter may generate secondary radiation that may include energetic photons (e.g., x-ray or gamma radiation) or other energetic particles (e.g., leptons, baryonic matter, or mesons).

As used herein, differential protection, shielding, or attenuation refers to shielding (e.g., quantified by a local attenuation value or an areal mass density) by laterally displaced different sections of the garment or device). Each of the different section of the garment is configured to cover, and thus to shield from radiation, a different region of a surface of the body.

The attenuation by a section of the device may be configured to complement self-shielding by the body of an interior region of the body. Self-shielding corresponding to surface region of the body refers to herein as attenuation by (or areal density of) internal structure that lies between that surface region and the interior region.

For example, a total shielding in the form of a total attenuation value or areal density value may be predetermined for one or more different interior regions of the body (e.g., based on a known or suspected health-related effect of radiation on that interior region). Self-shielding from radiation by intervening interior structure of the body (e.g., tissue or other internal structure) between the interior region and the surface region may be known, calculated, measured, or determinable by application of a combination of the above. The section of the device that shields that surface region is referred to as complementarily shielding the interior region when the combined attenuation by that section of the device and the self-shielding corresponding to the surface region that is shielded by that section provides at least the predetermined total required attenuation. For example, when the attenuation is quantified as an attenuation factor, the combined attenuation is determined by multiplying the self-shielding attenuation and the attenuation by that section of the device. When the attenuation is quantified as an areal density, the combined attenuation is determined by adding areal density of the self-shielding and the areal density of the section of the device.

As used herein, a garment refers to an item that may be worn on a body in the manner of an article of clothing (e.g., such as a vest, tunic, girdle, belt, sleeve, helmet, hat, or other similar wearable article), whether or not such an item would be worn otherwise as an article of clothing (e.g., when radiation shielding is not required). For example, the device may include a plurality of separately wearable and removable garments that may be worn in layered fashion, with outer garment layers worn over one or more inner garment layers. In some cases, a single garment layer may include multiple connected layers of material. The garments are designed to be worn by a user, such as an astronaut in space either within or outside of (e.g., in an extravehicular activity from) a spacecraft.

Each garment layer of the radiation protection device includes a plurality of radiation shield elements that are incorporated into a flexible substrate. A flexible substrate includes a material that may be fashioned into a garment. The flexible material is sufficiently flexible or elastic such that when fashioned into a garment and worn by a person, the garment is capable of bending together with a part of the person that is bent during performance of one or more anticipated tasks.

A shield element may include a solid material or a liquid that is confined to a compartment or container. Typically, the density of material in the shield element is sufficiently greater than the density of the flexible substrate such that attenuation by the flexible substrate is negligible (e.g., insignificant with regard to prediction of the likelihood of occurrence of a radiation-induced condition).

Each shield element is configured to attenuate one or more types of ionizing radiation that pass through that shield element. As used herein, a shield element is referred to as being incorporated into the substrate when an independently manufactured shield element is attached to or incorporated into a separately manufactured substrate, when a substrate is manufactured with shield elements that are embedded, inlaid, or otherwise incorporated into the substrate, or when a shielding liquid is contained within a compartment. For example, the flexible substrate may include a fabric or a foamy material (e.g., a foamy plastic material) that may be fashioned into a garment. The flexible substrate may include a flexible plastic that is provided with compartments that are fillable with a liquid, or with a bag, sack, pouch, bottle, or other container that is filled with a liquid. The flexible substrate may include structure to enable or facilitate attachment or incorporation of the shield elements to the flexible substrate. Such structure may include indentations, pockets, sleeves, pouches, loops, hooks, a surface of a hook-and-loop fastener, an adhesive or tacky surface, a ferromagnetic surface, or other attachment structure.

The shield elements are designed to absorb or otherwise provide shielding from the type of radiation that is expected to be encountered during travel outside of the protection provided by Earth's atmosphere and magnetic field. Such radiation may include energetic protons, or other ions or other charged particles. In order to shield against such radiation, the shield elements may include dense hydrocarbons (e.g., plastics), water, or other materials that are rich in hydrogen and other light nuclei. The radiation may include high energy ions, neutrons, gamma rays, or other high-energy photons or charged particles. In order to shield against such radiation, the shield elements may include an electron-rich material, such as a dense metal with a high atomic number (e.g., lead).

The configuration of the shield elements of the radiation protection device may be designed in consideration of the sensitivity to radiation of the part or organ of the body that each part of the radiation protection device is configured to cover and shield. For example, interior regions (e.g., tissue types or organs) of the body that may require a relatively large amount of shielding (so as to provide relatively large attenuation of radiation that is directed toward those regions) may include those interior regions that are rich in hematopoietic stem cells, other tissue-resident stem cells, or tissues or organs that have been found to be especially sensitive to a one or more types of incident radiation. Such regions may include, for example, ovaries, lungs, colon, breasts, stomach, iliac bone marrow, or other tissues that require increased protection (e.g., as per recommendations of the International Commission on Radiological Protection). Such interior regions are herein referred to as radiation-sensitive regions.

Interior regions that require increased protection may include organs, or in some cases, stem cell niches in organs or elsewhere that tend to have an increased concentration of tissue-resident stem cells. For example, distal airways of the lung may be rich in distal airway stem cells and the ileum section of the small intestine may be rich in LGR5+ stem cells. Protecting such interior regions may enable tissue regeneration following acute exposure to radiation, while protecting against cancer of that organ (since preventing a mutation in a stem cell may be equivalent to preventing a mutation in thousands of daughter cells).

Stem cell niches may include one or more types of stem cells. For example, the stem cells may include one or more of hematopoietic stem cells, distal airway stem cells, mesenchymal stem cells, Sca-1 stem cells, CD34+ hematopoietic stem cells, spermatogonia, intestinal LGR5+ stem cells, p63+Krt5+ stem cells, ovarian primordial follicle stem cells, thyroid progenitor cells, CD 133 progenitor cells, and endothelial progenitor cells.

The configurations of shield elements in different parts of the radiation protection device may differ from one another in one or more characteristics. For example, the shape, size, composition, distribution (e.g., density), structure, or other characteristics of shield elements in one part of the radiation protection device may differ from those characteristics in another part of the radiation protection device. Similarly, the characteristics of the shield elements (and of the flexible substrate) may differ from layer to layer of the radiation protection device.

For example, a distribution of number of layers of shielding (e.g., of shield elements incorporated into a substrate) among different sections of the radiation protection device may be determined by the degree of protection (e.g., quantified by attenuation of incident radiation) that is to be provided to a surface region of the body that is covered by that section. A section of the radiation protection device that is configured to be worn over an interior region of the body requiring greater protection from radiation may include more layers of shielding than a section of the radiation protection device that is configured to be worn over an interior region of the body requiring less protection. The thicknesses of the shield elements within a single layer may also be varied in order to provide variable selective shielding to different interior regions.

A radiation protection device, in accordance with an embodiment of the present invention, is sufficiently flexible to enable at least limited movement by a person who is wearing the device. The movement may enable sufficient range of motion so that the person may be able to perform anticipated tasks while wearing the radiation protection device (e.g., bend a torso or limb through a predetermined bending angle. For example, a section of the radiation protection device may be configured to be compressed on one side of the device while a corresponding opposite (e.g., on an opposite side of the limb or torso) section is configured to be stretched. The shield elements may be arranged on the flexible substrate such as to not impede bending of the flexible substrate. In this case, a gap between shield elements on one layer may be covered and shielded by shield elements on one or more other layers of the radiation protection. Layers of the radiation protection device may be configured to slide relative to one another so as to further enable bending of the torso or limb.

A radiation protection device that provides selective protection from ionizing radiation may be advantageous over a device that provides non-selective protection. A radiation suit or similar device could be configured to provide an approximately constant adequate radiation protection (e.g., suitable for the most sensitive interior region of the body) to all parts of the body. Such a device could be so massive as to severely impair or restrict mobility or maneuverability of person wearing the device, as well as increasing the thrust required to launch or propel a vehicle holding one or more of such devices (typically at least one device per passenger).

Active bone marrow is rich in blood-forming hematopoietic stem cells (HSC). HSC concentrations are present in marrow a several locations in the human body, including the hip, sternum, ribs, vertebrae, and skull. For example, in adults, the active bone marrow of the iliac bones of the hip may require more radiation protection than other parts of the body. On the other hand, the bone marrow in the skull provides the foremost concentration of active bone marrow in early life and may therefore require more protection.

Therefore, the distribution of radiation attenuation in a radiation protection device may be configured in accordance with the age of an intended user. The distribution of radiation protection for different interior regions of the body may be configured by configuring the type, thickness, and the distribution of radiation attenuating materials that are incorporated into the radiation protection device.

In some cases, the distribution of radiation attenuation in the radiation protection device may be configured to protect a predetermined fraction of active bone marrow in the body or in a particular interior region of the body. The protected quantity may be determined by consideration of the quantity of bone marrow that is typically transplanted into a patient to replace damaged or destroyed bone marrow. For example, the protected quantity of bone marrow may be in the range 25% to 150% of a typical quantity of transplanted bone marrow.

In some cases, the distribution of radiation attenuation in the radiation protection device may be configured to prevent mutations in organs, or regions of organs, that are rich in stem cells. Tissue-resident stem cells may be shielded by the radiation protection device. This may enable the regenerative capacity of the stem cells to enable the body to recover from deterministic effects of radiation. In this manner, cell damage that could otherwise lead to cancer or other radiation-induced conditions may also be averted.

In some cases, the distribution of radiation attenuating material in the radiation protection device may be configured in consideration of the inherent radiation attenuation due to various tissues (e.g., skin, bone, muscle, or adipose tissue) through which radiation would have to pass in order to reach bone marrow or other interior regions that require radiation protection. For example, the amount and distribution of radiation attenuating material needed may be determined using the formula $A_D(x, y, z) = A_R/A_T$, where $A_D$ is a required radiation attenuation to be provided by the radiation protection device at point x, y, z within the user's body, $A_R$ is the total required radiation attenuation at the point, and $A_T$ is the radiation attenuation provided by the surrounding or adjacent tissue.

The hematopoietic system is highly sensitive to ionizing radiation. Doses of 70 rad (0.7 Gy) and above may cause decreased hematocrit, neutropenia, and lymphopenia, leading to anemia and immune suppression. Major bone marrow cell loss may occur with doses of 150 rad (1.5 Gy) or more.

A radiation protection device, in accordance with an embodiment of the present invention, may be designed to attenuate one or more types of incident ionizing level to an acceptable level. The acceptable level may be determined in accordance with one or more effects of radiation on a person's body.

FIG. 1 schematically illustrates a radiation protection device, in accordance with an embodiment of the present invention.

Radiation protection device 10 is configured to be worn as one or more garments by a user 11. Radiation protection device 10 may include one or more separate garments that may be worn as layers one over another. In some cases, radiation protection device 10 may include a layered garment that incorporates multiple layers that may or may not be separable from one another.

As shown, radiation protection device 10 includes one or more garments in the form of a tunic. Other forms of garments are possible. For example, radiation protection device 10 may include one or more coats, aprons, hats, helmets, scarves, gloves, pants, skirts, capes, ponchos, vests, jackets, shirts, or other types of garments.

Each garment of radiation protection device 10 may include one or more structures to facilitate donning and removal, while preventing the garment from accidentally falling off of user 11. For example, a garment of radiation protection device 10 may include a closeable full-length or partial opening that may be opened to facilitate donning and removal. The opening may be provided with one or more closing or fastening structures that may be closed or fastened to retain the garment in place on user 11. For example, the closing or fastening structure may include one or more flaps, straps, buttons, snaps, laces, hook-and-loop fasteners, buckles, magnets, zippers, clasps, or other closing or fastening structure. In some cases, a garment of radiation protection device 10 may be configured to be donned or removed without opening any closing or fastening structure (e.g., may be pulled on over the head and raised arms of user 11).

Radiation protection device 10 is configurable to provide varying degrees of radiation protection (e.g., as quantifiable by radiation attenuation) or types of radiation protection (e.g., quantifiable by a ratio of attenuation of one type or energy of radiation to attenuation of another type or energy of radiation) to different parts of user 11. For example, one or more of a thickness of radiation protection device 10, a distribution of shield elements, a density, size, shape, or composition of shield elements, a number of layers, or another characteristic of radiation protection device 10 may vary from section to section of radiation protection device 10.

For example, a lower-protection section 10a of radiation protection device 10 may be thinner or otherwise provide lower attenuation than a higher-protection section 10b of radiation protection device 10. Characteristics of the radiation protection that is provided by radiation protection device 10 to each interior region of user 11 may be selected in accordance with a sensitivity of each interior region of user 11 to one or more types of radiation. For example, a more sensitive interior region of user 11 may have a relatively high concentration of stem cells, or may be otherwise more susceptible to mutagenesis, than another less sensitive interior region of user 11. Radiation protection device 10 may be configured such that, when worn by user 11, a higher-protection section 10b covers the more sensitive interior region and a lower-protection section 10a covers the less sensitive interior region.

For example, in some cases, lower-protection section 10a may have an areal density of about 7 $g/cm^2$. A higher-protection section 10b may have an areal density of about 19 $g/cm^2$. Other ranges may be appropriate for different individuals (e.g., with different body shape or different sensitivity to radiation) or for different anticipated exposure to radiation. For example, in some cases a minimum areal density of a lower-protection section 10a may be in the range from 0.1 $g/cm^2$ to 20 $g/cm^2$. A maximum areal density of higher-protection section 10b may be in the range from 4 $g/cm^2$ to 46 $g/cm^2$.

For example, the energy spectrum of particles that are emitted during large solar particle events has been measured to range from 20 MeV to 300 MeV. A 20 MeV proton at the low end of the spectrum may have a range of about 4.2 mm in water. A 100 MeV proton may have a range in water of about 76 mm. A 200 MeV proton may have a range in water of about 260 mm. A 300 MeV proton at the high end of the spectrum may have a range in water of about 510 mm. Thus, shielding that includes materials that are rich in hydrogen but denser than water may be useful as at least an inner garment layer of radiation protection device 10. Furthermore, limiting the protection to those interior regions of the user 11 that are most sensitive to the effects of radiation may enable effective protection without excessively increasing the mass or thickness of radiation protection device 10.

The degree of sensitivity to radiation of different interior regions of user 11 may vary from individual to individual. For example, sensitivity of an interior region of user 11 to one or more types of radiation may by affected by an age and sex of user 11, by a medical history of user 11, or by a health-related condition. For example, sensitivity of an interior region may be affected by current or past diseases or injuries, previous exposure to ionizing radiation, pregnancy or lactation, genetic predispositions, past or current exposure to various environmental conditions, diet, past or current medications or treatments, level of activity, or other conditions. Sensitivity of an interior region of user 11 may be determined by stem cell content or concentration, or by a fraction of cells in that interior region that are dividing.

Radiation protection device 10 may be configured to enable user 11 to move in a manner that is appropriate to planned activities of user 11. For example, radiation protection device 10 may be configured to enable at least limited (e.g., sufficient to enable a planned activity) bending of a torso, one or more limbs, or another part of user 11. For example, rigid shield elements of a garment of radiation protection device 10 may be embedded or otherwise incorporated into a flexible or elastic substrate. The sizes and shapes of rigid shield elements, as well as the separation distance between adjacent rigid shield elements, may be configured to enable a predetermined degree of bending (e.g., maximum curvature) of the garment. The flexible substrate may deform in various ways to allow compression or stretching to accommodate bending of the radiation protection device 10 and to ensure freedom of movement of user 11. Layers of radiation protection device 10 may be configured to slide past one another to facilitate bending of radiation protection device 10. At least some of the shield elements may be pliable to at least a limited extent (e.g., liquid-filled sacs or bags).

In some cases, radiation protection device 10 may be configured to be integrated into shielding of a spacecraft or cabin. For example, at times when radiation protection device 10 need not be worn by user 11 (e.g., when no solar particle event is occurring), radiation protection device 10 may be removed and stowed. Walls of the cabin or spacecraft may be configured such that radiation protection device 10 may be attached to the wall. For example, the wall may be provided with clips or other structure that facilitate attachment of radiation protection device 10 to the wall. When attached to the wall, radiation protection device 10 may provide additional protection to the interior of the spacecraft or cabin, e.g., from galactic cosmic radiation or other radiation.

In accordance with an embodiment of the present invention, radiation protection device 10 may include several layers of protective garments.

Figure 2:
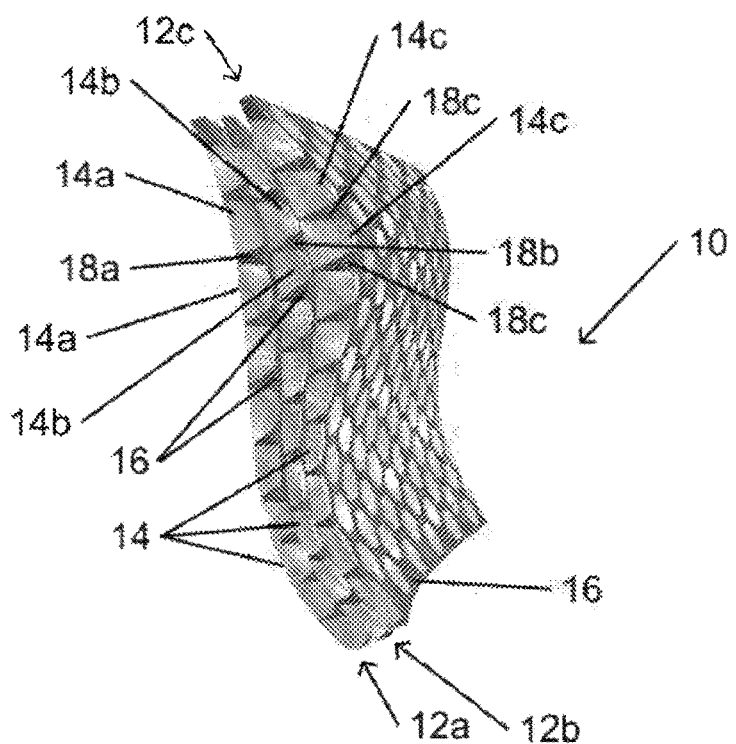
FIG. 2 schematically illustrates garment layers of the radiation protection device shown in FIG. 1.

FIG. 2 schematically illustrates garment layers of a section of the radiation protection device shown in FIG. 1.

Radiation protection device 10 includes three garment layers: inner garment layer 12a, middle garment layer 12b, and outer garment layer 12c. A radiation protection device 10 may include less than three layers or more than three layers.

The thickness of each garment layer may not be constant. The thickness of any particular layer may vary in order to provide selective shielding to different surface regions of the body. Alternatively, selective coverage may be achieved by stacking additional layers over particular surface regions.

In some cases, each pair of adjacent garment layers (e.g., inner garment layer 12a and middle garment layer 12b or middle garment layer 12b and outer garment layer 12c) may be free to slide relative to one another. Such free sliding may facilitate bending or other movement of user 11. For example, the facing surfaces of the pairs of adjacent layers may be free of any projections or indentations that could impede lateral movement of one layer relative to another. The facing surfaces may be configured (e.g., with a nonstick coating) to facilitate relative sliding between the adjacent layers. For example, one or more of the facing surfaces may be made of, or coated with, one or more friction reducing materials. Such materials may include, for example, polytetrafluoroethylene, polyamide-imide, nylon 6-6, nylon 4-6, graphite, graphite powder, acetal homopolymer, carbon fiber, or another friction-reducing material. In some cases, the innermost and outermost surfaces (e.g., an inward-facing surface of inner garment layer 12a or an outward-facing surface of outer garment layer 12c) may be configured so as to prevent snagging or friction between radiation protection device 10 and any surface (e.g., skin or clothing) under inner garment layer 12a or over (e.g., a protective suit for extravehicular activity) outer garment layer 12c.

Each of the inner garment layer 12a, middle garment layer 12b, and outer garment layer 12c includes a plurality of shield elements 14 that are incorporated into a flexible substrate 16. For example, shield elements 14 may be embedded in flexible substrate 16, as shown in FIG. 2. Alternatively or in addition, shield elements 14 may be attached to a surface (e.g., an outer surface) of flexible substrate 16, inserted in a pocket or sleeve of flexible substrate 16, or otherwise attached to flexible substrate 16.

Shield elements 14 may be configured to attenuate one or more types of radiation. For example, in order to attenuate ionizing radiation in the form of energetic particles (e.g., solar wind particles, galactic cosmic ray particles, or other ions, neutrons, or other particles), shield elements may include materials that are composed of light nuclei (e.g., hydrogen, carbon, oxygen, or other light nuclei). For example, shield elements 14 may include polyethylene, polypropylene, or another hydrocarbon, water, or another material composed primarily of elements having a low atomic mass. In order to attenuate ionizing radiation in the form of energetic photons (e.g., x-rays or gamma rays, e.g., resulting from interaction of energetic charged particles with matter), shield elements 14 may include a material with a high atomic number. For example, shield elements 14 may include a metal (e.g., lead, gold, silver, tungsten, or another metal) or a metallic alloy in the form of a powder, pellets, coating, lining, layer, or another form. For example, a powder or pellet may have a particle diameter or other characteristic dimension in the range from less than a micrometer to about a millimeter.

In some cases, shield elements 14 may have a composition that is similar to that of flexible substrate 16. However, the density of the material of shield elements 14 may be denser than that of flexible substrate 16. For example, shield elements 14 may include high density polyethylene, while flexible substrate 16 includes low density polyethylene (e.g., polyethylene foam or fabric).

Each shield element 14 may be separated from an adjacent shield element 14 by a section of flexible substrate 16 forming a gap. Shield elements 14 in inner garment layer 12a, middle garment layer 12b, and outer garment layer 12c may be configured such that a shield element 14 in one of the layers covers a gap in another of the layers. Thus, inner garment layer 12a, middle garment layer 12b, and outer garment layer 12c of radiation protection device 10 may be configured such that all surface regions of a user 11 that are covered by radiation protection device 10 are protected from incident radiation.

For example, shield elements 14a in inner garment layer 12a are separated by a gap 18a. Similarly, shield elements 14b in middle garment layer 12b are separated by a gap 18b that is approximately aligned laterally to overlie gap 18a. However, in outer garment layer 12c, shield element 14c overlies approximately aligned gaps 18a and 18b. Thus, a surface region of the body of a user 11 underlying approximately aligned gaps 18a and 18b may be protected by shield element 14c. Similarly, a surface region of the body of a user 11 that underlies gaps 18c in outer garment layer 12c may be protected by shield elements 14b and 14a that underlie gaps 18c.

In some cases, user 11, or a cabin, spacecraft, space suit, or other enclosure surrounding user 11, may be provided with one or more dosimeters or other radiation sensors. For example, the radiation sensor may measure a radiation level in an area where user 11 is found. The radiation sensor may measure the level of radiation that is incident on one or more interior regions of the body of user 11. The result of the radiation measurement may be utilized in determining whether or not radiation protection device 10 need be worn, the recommended type of garment of radiation protection device 10 that is to be worn (e.g., when more than one type is available), and the number and selection of garment layers of radiation protection device 10 that are recommended to be worn.

In accordance with an embodiment of the present invention, shield elements 14 may be embedded or inlaid in flexible substrate 16, e.g., in the form of a flexible matrix or foam.

Figure 3A:
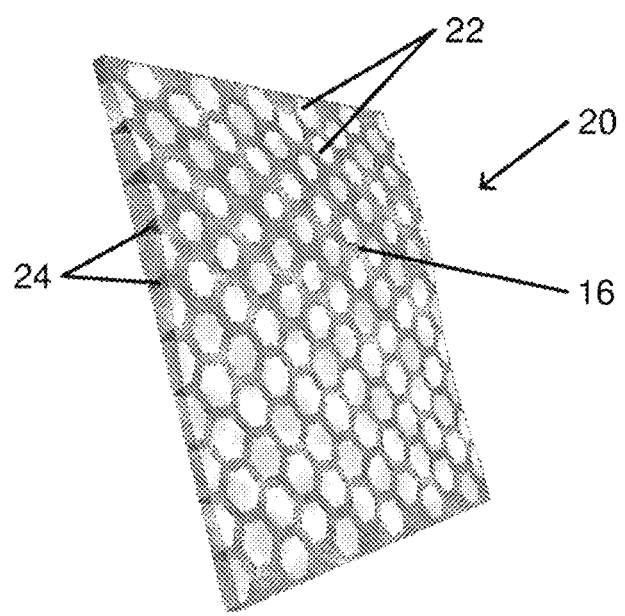
FIG. 3A schematically illustrates a garment layer of a radiation protection device with shield elements that are embedded in a flexible substrate, in accordance with an embodiment of the present invention.

FIG. 3A schematically illustrates a layer of a radiation protection device with shield elements that are embedded in a flexible substrate, in accordance with an embodiment of the present invention.

In radiation protection garment 20, a section of which is shown in FIG. 3A, embedded shield elements 22 are embedded in flexible substrate 16. For example, each embedded shield element 22 may be in the form of substantially rigid plug. Each plug is at least partially surrounded by a flexible and elastic material forming flexible substrate 16.

Embedded shield elements 22 and flexible substrate 16 of radiation protection garment 20 may be produced by application of one or more molding, extrusion, injection, machining, or adhesion or other production processes. For example, embedded shield elements 22 may be molded or machined out of a substantially rigid material. Embedded shield elements 22 may be positioned in a fixture into which material for forming flexible substrate 16 may be injected. As another example, openings or indentations for accommodating embedded shield elements 22 may be punched or otherwise machined out of a layer of material forming flexible substrate 16. Plugs of substantially rigid material for forming embedded shield elements 22 may be inserted into the openings or indentations and caused to adhere to flexible substrate 16.

For example, embedded shield elements 22 may include high-density polyethylene. Flexible substrate 16 may include polyethylene foam. Alternatively or in addition, flexible substrate 16 may include another type of material that is sufficiently thick so as to incorporate embedded shield elements 22 but sufficiently flexible or elastic so as enable bending of radiation protection garment 20.

Alternatively or in addition, embedded shield elements 22 or flexible substrate 16 may include a polymeric mixture that includes one or more of polyurethane, polyamide, polyvinyl chloride, polyvinyl alcohol, natural latex, polypropylene, ethylene vinyl acetate, polyester, or another polymer. One or more components may include an additive to improve the flexibility, strength, durability, or another property of the polymeric mixture or to ensure that the polymeric mixture has an appropriate uniformity and consistency. For example, an additive may include a plasticizer (e.g., epoxy soybean oil, ethylene glycol, propylene glycol, or another plasticizer), an emulsifier, a surfactant, a suspension agent, a leveling agent, a drying promoter, a flow enhancer, or other additive. A radiation attenuating material included in embedded shield elements 22 may include one or more of carbon nano-materials with absorbed hydrogen, metal hydrides such as LiH, $MgH_2$, $LiBH_4$, $NaBH_4$, $BeH_2$, $TiH_2$ or $ZrH_2$, palladium (and alloys) with absorbed hydrogen, hydrocarbons (polyethylene or $(CH2)_n$) with boron, quasi-crystals (e.g., TiZrNi), condensed hydrogen (solid and liquid), water ($H_2O$), drinking water, cooling liquid, and other hydrogen rich materials or mixtures such as urine.

A particular isotope of an element may be selected for the shielding material in some cases. For example, a particular isotope may have a relatively (e.g., to other isotopes) large nuclear cross section for a particular nuclear reaction. For example, boron-10 has a high cross section for neutron capture.

Hydrogen is unique in its interaction with high-energy nuclei components of galactic cosmic rays which have an electric charge greater than +2 because it cannot fragment into smaller nuclei. Polyethylene ($C_2H_4$) n contains 14% hydrogen by mass fraction. Therefore, nano-material composites using a polyethylene matrix are particularly attractive as a primary component in a novel shielding material. A number of nano-material additives are suitable for loading this and other matrices. Such additives may include carbon nanostructures (fullerenes, nanotubes, graphene, nano-onions), metal hydride nanoparticles (including LiH, $LiBH_4$, $BeH_2$), boron nitride/boron carbide nanoparticles (offer both good strengthening characteristics as well as neutron absorption), alkylated-fluorinated nanotubes (to promote dispersion within the matrix and increase mechanical properties), graphene nanoplatelets (carbon nanotube co-reinforced high-density polyethylene composites), and high-density polyethylene fibers woven with carbon nanotube yarn (to form flexible deployable radiation shielding blankets).

For example, embedded shield elements 22 may be rigid and substantially incapable of being bent by forces that are typically exerted by a person who is wearing radiation protection garment 20. Each embedded shield element 22 may have a tapered profile (e.g., a profile with an approximately trapezoidal shape). Thus, a separating strip 24 of flexible substrate 16 that separates adjacent embedded shield elements 22 may have a wedge-like profile.

For example, each embedded shield element 22 may have an inward-facing surface with a surface area that is greater than the surface area of an opposite, outward-facing surface. Thus, a separating strip 24 of flexible substrate 16 that separates adjacent embedded shield elements 22 may form a tapering gap (e.g., with an approximately triangular, wedge-like profile, or other tapering profile).

For example, radiation protection garment 20 may be formed by placement of shielding elements to form embedded shield elements 22 in an arrangement that corresponds to the positions of embedded shield elements 22 in radiation protection garment 20. Spaces or gaps that are formed in between the shield elements may be fully or partially filled with a flexible material (e.g., a polymer foam or other flexible material) to form flexible substrate 16 in the form a matrix of the flexible material.

The flexibility and elasticity of flexible substrate 16 and of separating strips 24 may radiation protection garment 20 with sufficient flexibility to enable radiation protection garment 20 to bend together with a person who is wearing radiation protection garment 20.

Figure 3B:
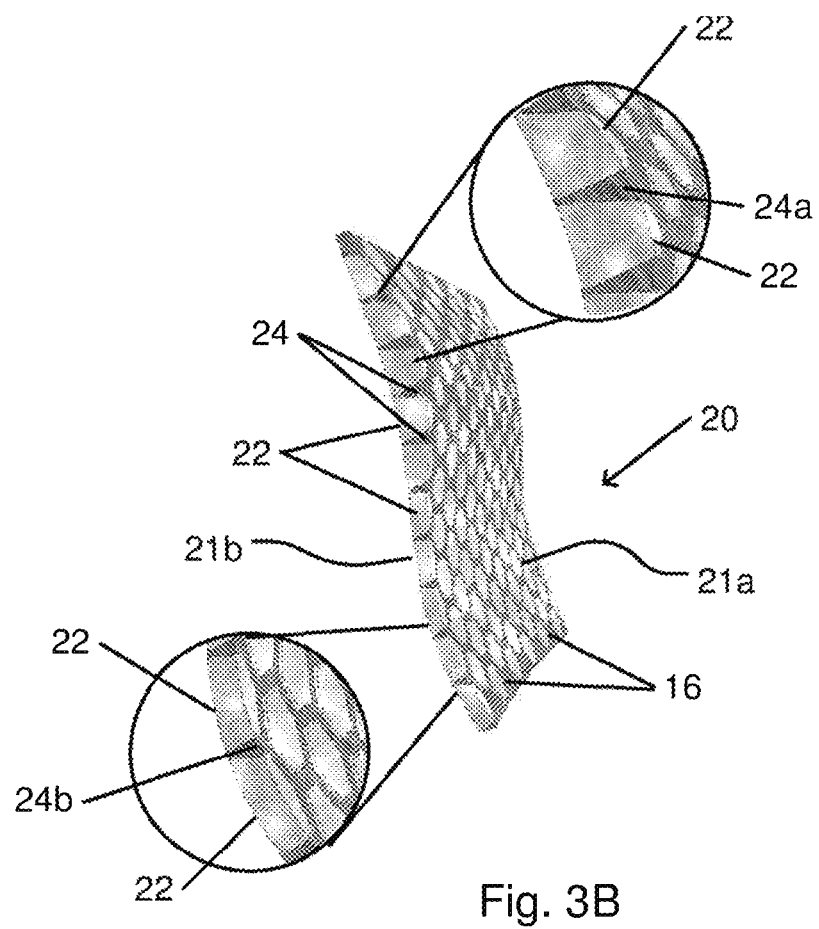
FIG. 3B schematically illustrates bending of the garment layer shown in FIG. 3A.

FIG. 3B schematically illustrates bending of the garment layer shown in FIG. 3A.

When a section of radiation protection garment 20 is bent, the opening angle of the wedge-like profile of separating strips 24 may increase or decrease.

For example, when a section of radiation protection garment 20 is bent such that surface 21a of radiation protection garment 20 is locally convex and surface 21b is locally concave, separating strips 24 in that section may be stretched widthwise. When, stretched widthwise, the opening angle of the wedge-like profile may be increased, as shown for stretched separating strip 24a. Similarly, when a section of radiation protection garment 20 is bent such that surface 21a of radiation protection garment 20 is locally concave and surface 21b is locally convex, separating strips 24 in that section may be compressed widthwise. When, compressed widthwise, the opening angle of the wedge-like profile may be decreased, as shown for compressed separating strip 24b.

Two or more radiation protection garments 20 may be worn as layers over one another.

Figure 4C:
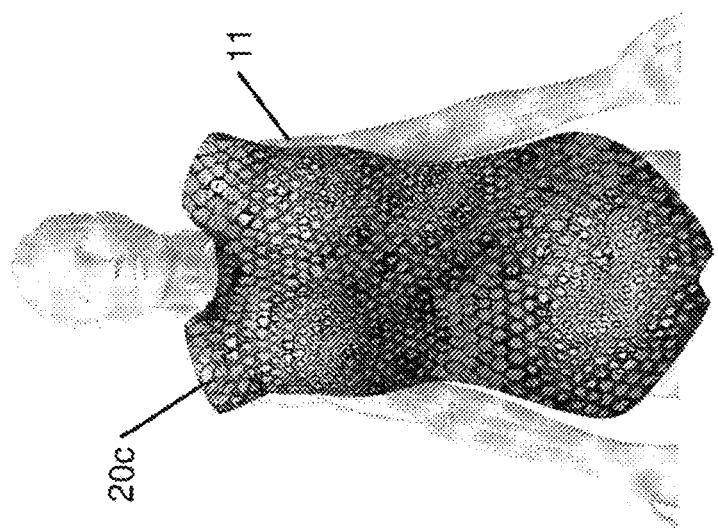
FIG. 4C schematically illustrates an outer garment layer with embedded shield elements worn over the garment layers shown in FIG. 4B.
Figure 4B:
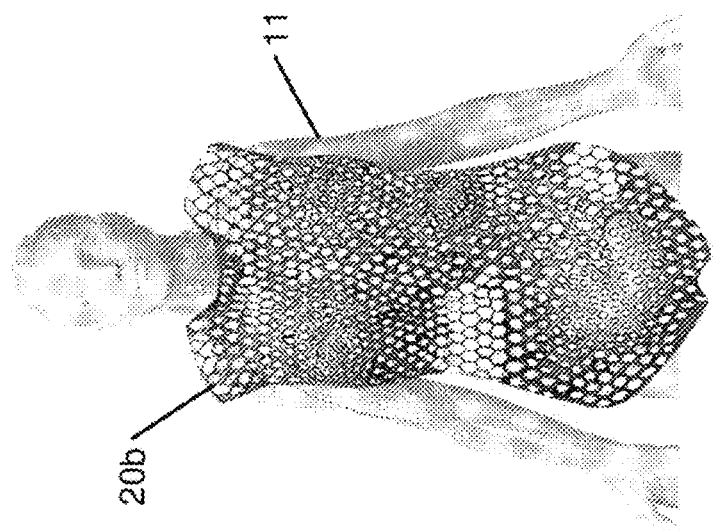
FIG. 4B schematically illustrates a middle garment layer with embedded shield elements worn over the inner garment layer shown in FIG. 4A.
Figure 4A:
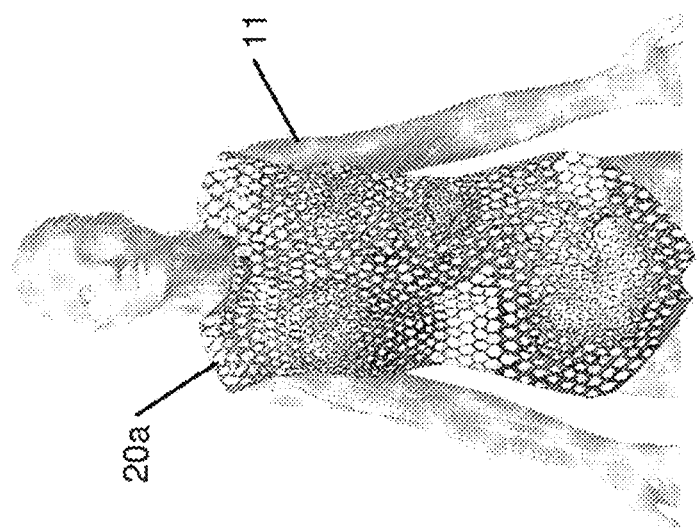
FIG. 4A schematically illustrates an inner garment layer with embedded shield elements of a radiation protection device, in accordance with an embodiment of the present invention.

FIG. 4A schematically illustrates an inner garment layer with embedded shield elements of a radiation protection device, in accordance with an embodiment of the present invention. FIG. 4B schematically illustrates a middle garment layer with embedded shield elements worn over the inner garment layer shown in FIG. 4A. FIG. 4C schematically illustrates an outer garment layer with embedded shield elements worn over the garment layers shown in FIG. 4B.

For example, inner radiation protection garment 20a may be worn directly over personal clothing (e.g., the clothing worn when no radiation protection is required) or skin of user 11. Middle radiation protection garment 20b may be worn over inner radiation protection garment 20a. Outer radiation protection garment 20c may be worn over middle radiation protection garment 20b. When all of the garment layers are worn, embedded shield elements 22 on the different garment layers may be so aligned with one another as to provide a predetermined degree of protection (e.g., attenuation) to all covered parts of user 11.

In accordance with an embodiment of the present invention, a garment of a radiation protection device may include one or more sheets of shield elements in the form of sequins. The flexible substrate to which the shield elements are attached may include a sheet of flexible material to which the shield elements are attached, or flexible webbing that connects the shield elements to one another.

In accordance with an embodiment of the present invention, a garment of a radiation protection device may include shield elements in the form of packets of a liquid. The packets may be inserted into pockets or sleeves in a flexible substrate.

FIG. 5A schematically illustrates an inner garment layer of a radiation protection device, the layer having shield elements in the form of sequins, in accordance with an embodiment of the present invention. FIG. 5A schematically illustrates an inner garment layer of a radiation protection device, the garment layer having shield elements in the form of sequins, in accordance with an embodiment of the present invention. FIG. 5B schematically illustrates a middle garment layer with shield elements in the form of sequins and worn over the inner garment layer shown in FIG. 5A.

For example, inner sequined radiation protection garment 30a may be worn directly over personal clothing or skin of user 11. Middle sequined radiation protection garment 30b may be worn over inner sequined radiation protection garment 30a.

FIG. 5C schematically illustrates an outer garment layer with liquid shield elements worn over the garment layers shown in FIG. 5B.

Liquid-fillable radiation protection garment 32 may be worn over middle sequined radiation protection garment 30b. Liquid-fillable radiation protection garment 32 includes a plurality of bag holders 34. For example, each bag holder 34 may be in the form of a sleeve or pocket into which a liquid bag 38 may be inserted. Each bag holder 34 may be provided with bag retaining structure 36 that is configured to prevent accidental or unintentional removal of a liquid bag 38 from bag holder 34. For example, bag retaining structure 36 may include a sealable flap, strap, or lip. Bag retaining structure 36 may be provided with a button, zipper, snap, hook-and-loop fastener, magnet, adhesive or tacky surface, or other structure to hold closed bag retaining structure 36.

Bag holders 34 may be made of a flexible material to form a flexible substrate of liquid-fillable radiation protection garment 32. Similarly, liquid bags 38 may be made of a flexible material. In some cases, the material of bag holders 34, of liquid bag 38, or of both may be elastic.

Liquid bag 38 may be filled with water or another liquid. For example, liquid-fillable radiation protection garment 32 may be utilized for storage of potable water for drinking, e.g., during extravehicular activity or as an emergency supply when other sources of drinking water are unavailable. Liquid bag 38 may be filled with urine or other wastewater. For example, liquid-fillable radiation protection garment 32 may be used to temporarily store wastewater for later purification by a purification device. Liquid bag 38 may be filled with another liquid.

Liquid layer sections 50 of liquid-fillable radiation protection garment 32 may be configured as a plurality of stacked liquid-fillable layers. For example, liquid layer sections 50 may be configured such that radiation traverses a greater distance through (or, equivalently, a greater areal density of) a liquid filling liquid-fillable radiation protection garment 32 than another section of liquid-fillable radiation protection garment 32. For example, a liquid layer section 50 may be designed to be worn over an interior region of elevated sensitivity to radiation (e.g., more sensitive than other interior regions of user 11, such as a stem cell niche or other interior region of higher sensitivity) of user 11.

Figure 5D:
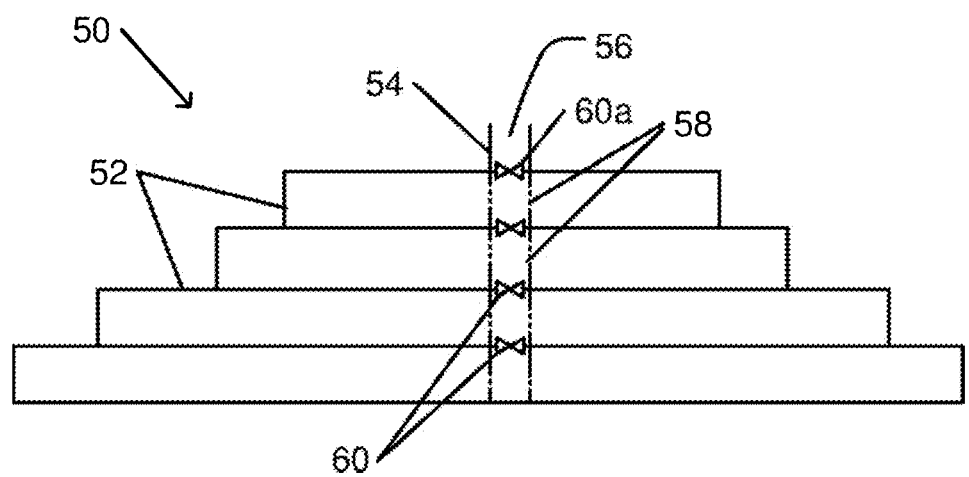
FIG. 5D schematically illustrates a cross section of a liquid layer section of the outer garment layer with liquid shield elements shown in FIG. 5C.

FIG. 5D schematically illustrates a cross of a liquid layer section of the outer garment layer with liquid shield elements shown in FIG. 5C.

Liquid layer section 50 includes a plurality of liquid-fillable compartments 52 that are stacked atop one another.

Each liquid-fillable compartment 52 of liquid layer section 50 may be in the form of a bag or pouch of a flexible or elastic material. Tube 54 may provide support for maintaining a shape of liquid layer section 50. In addition, tube 54 may be used to fill one or more liquid-fillable compartments 52, or to remove liquid from one or more liquid-fillable compartments 52. For example, tube 54 may be made of a durable material with limited flexibility, such as polyethylene, polypropylene, another thermoplastic, another polymer, carbon fiber, a metal, or another material that is suitable for forming a tube that provides support or liquid access.

Tube 54 may be used to conduct liquid from tube opening 56 to one or more liquid-fillable compartments 52. Tube opening 56 may be accessible from outside of liquid-fillable radiation protection garment 32. In some cases, tube opening 56 may be provided with a cap or other closure that may be opened in order to access tube opening 56. For example, the cap or closure may be configured to pad or cover tube opening 56 in order to prevent any damage or injury that could occur by a collision with tube opening 56.

For example, tube 54 may be provided with one or a plurality of liquid-permeable segments 58 that are configured to enable flow of liquid between tube 54 and a corresponding one or a plurality of liquid-fillable compartments 52. For example, a liquid-permeable segment 58 may include perforations or openings to enable liquid to flow between tube 54 and a liquid-fillable compartment 52. Alternatively or in addition, a liquid-permeable segment 58 may include a porous material to enable flow of liquid between tube 54 and a liquid-fillable compartment 52.

For example, prior to use of liquid-fillable radiation protection garment 32, a liquid may be introduced into one or more liquid-fillable compartments 52 via tube opening 56 and tube 54. When liquid layer section 50 is to be emptied, or when liquid in a liquid-fillable compartment 52 is withdrawn for drinking or for another purpose, the liquid may be removed from liquid-fillable compartments 52 via tube 54 and tube opening 56.

Tube 54 may be provided with one or more valves 60. Each valve 60 may be normally shut (e.g., preventing flow of liquid in either direction). In this case, a valve 60 may be opened by application of inward pressure to tube opening 56 (e.g., to introduce a liquid into liquid-fillable compartments 52 via valves 60), or by application of suction to tube opening 56 (e.g., to suck liquid out of liquid-fillable compartments 52 via valves 60) or pressure to one or more liquid-fillable compartments 52 (e.g., to squeeze liquid out of liquid-fillable compartments 52). In some cases, a valve 60 may be directional valve that enables substantially unimpeded flow in one direction while preventing or impeding flow in the opposite direction. In some cases, a valve 60 may be opened by insertion of a rod or tube (e.g., straw) into valve 60 via tube opening 56, by application of a lateral (e.g., lateral squeezing force) to valve 60, or by other structure that is configured to enable control over opening or closing of a valve 60.

For example, in some cases, a valve 60 (such as valve 60a) may be provided to control flow of liquid into or out of tube 54 via tube opening 56. In some cases, a valve 60 may be located between liquid-permeable segments 58 that connect to different liquid-fillable compartments 52. For example, such valves 60 may be utilized to selectively fill or withdraw liquid from one or more selected liquid-fillable compartments 52.

Use of water to fill liquid bag 38 may be advantageous. Water may be effective at attenuating radiation in the space environment. Water also serves multiple purposes and is necessary for manned space missions. Its dual usage as a radiation attenuating material is favorable from a payload perspective. Water is always included in crew modules of space vehicles and in space suits.

A sequined radiation protection garment, such as inner sequined radiation protection garment 30a, middle sequined radiation protection garment 30b, or another sequined radiation protection garment, may be configured to attenuate radiation while enabling flexibility. The flexibility may be sufficient to enable user 11 to bend so as not impede user 11 in the performance of a one or more anticipated tasks. The sequined radiation protection garment may include one or more flexible sheets of sequins. As used herein, a sequin refers to any solid object that may be incorporated with a plurality of similar objects into a garment. For example, the sequins may include objects that are similar to buttons, medallions, beads, studs, naps, or similar objects.

Figure 6C:
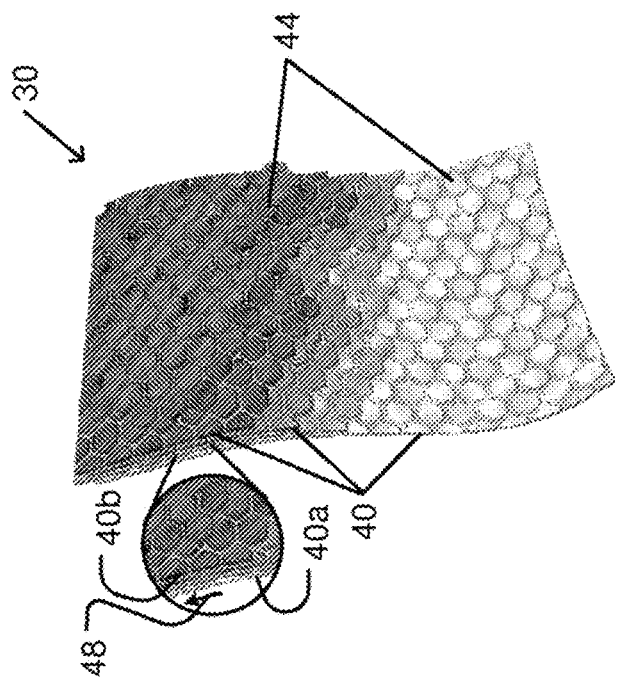
FIG. 6C schematically illustrates bending of the sequin shield element garment layer shown in FIG. 6B.
Figure 6B:
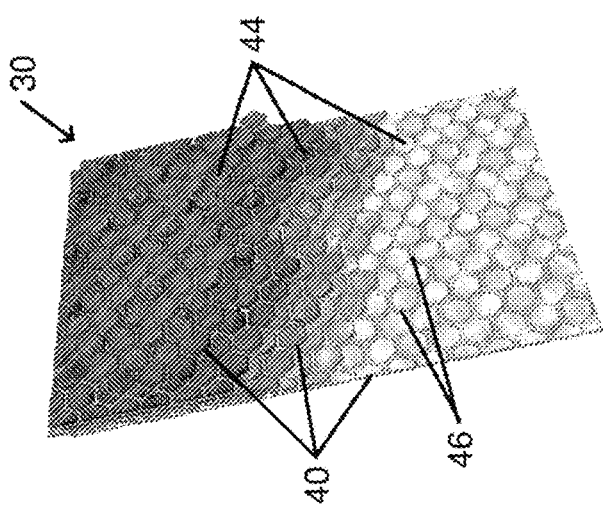
FIG. 6B schematically illustrates multiply layered sheets of the sequin shield element garment layer shown in FIG. 5A.
Figure 6A:
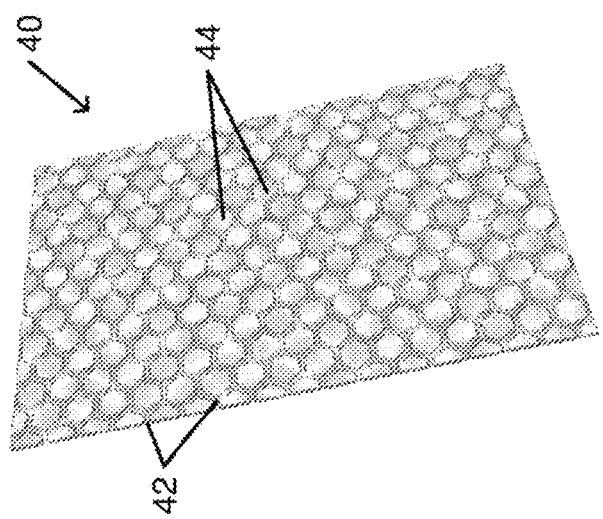
FIG. 6A schematically illustrates a sheet of the sequin shield element garment layer shown in FIG. 5A.

FIG. 6A schematically illustrates a sheet of the sequin shield element garment layer shown in FIG. 5A.

Sequin sheet 40 includes a flexible sequin substrate 42 to which a plurality of shield sequins 44 are attached.

For example, flexible sequin substrate 42 may consist of a natural or synthetic fabric. For example, flexible sequin substrate 42 may include a woven or otherwise produced fabric that enables at least limited passage of air or gasses. Alternatively or in addition, flexible sequin substrate 42 may include a film, foam, or other flexible material. Flexible sequin substrate 42 may include a polyethylene fabric. Alternatively or in addition, flexible sequin substrate 42 may include a polymeric fabric, such as polychloroprene (e.g. neoprene), polypropylene, aramid fiber, rayon, nylon, or another polymeric fabric.

Flexible sequin substrate 42 may be in the form of a continuous sheet to which shield sequins 44 are attached. For example, shield sequins 44 may be attached to flexible sequin substrate 42 by tying on, sewing or weaving, glue or other adhesive, welding, magnets, staples, screws, rivets, clips, or otherwise. Alternatively or in addition, flexible sequin substrate 42 may be in the form of webbing that connects edges of shield sequins 44 to one another. For example, flexible sequin substrate 42 may be attached to edges of shield sequins 44 by sewing, adhesive, welding, or otherwise.

Shield sequins 44 may be sufficiently rigid so as not to bend during typical activity of a person wearing a garment that includes sequin sheet 40. Substantially all flexibility of sequin sheet 40 may be provided by flexible sequin substrate 42.

Shield sequins 44 may be hexagonally shaped as shown. Alternatively or in addition, some or all shield sequins 44 may be otherwise shaped (e.g., square, rectangular, triangular, polygonal, circular, oval, or another shape). In some cases, hexagonally shaped shield sequins 44 may enable an optimum balance between coverage of sequin sheet 40 by shield sequins 44 and flexibility of sequin sheet 40.

Each shield sequin 44 is configured to attenuate one or more types of ionizing radiation. For example, shield sequins 44 may be configured to attenuate radiation in the form of energetic particles. Thus, shield sequins 44 may include a solid material with a high density of light nuclei, such as high-density polyethylene. Alternatively or in addition, may include another solid polymer, hydrocarbon, or other material with a high density of light. In some cases, shield sequins 44 may be configured to attenuate radiation in the form of high energy photons. In this case, shield sequins 44 may include a heavy metal or other material with a high atomic number. In some cases, shield sequins 44 may be configured to attenuate both particulate and photonic radiation. For example, shield sequins 44 may include metallic powder or particles that are embedded in a solid polymer.

A sequined radiation protection garment, such as inner sequined radiation protection garment 30a or middle sequined radiation protection garment 30b, may include two or more layered sequin sheets 40.

FIG. 6B schematically illustrates multiply layered sheets of the sequin shield element garment layer shown in FIG. 5A.

A section of sequined radiation protection garment 30 includes a plurality of layered sequin sheets 40. Each sequin sheet 40 that overlies another sequin sheet 40 may be connected to that underlying sequin sheet 40 at one or more edges of the overlying sequin sheet 40. The connection of an overlying sequin sheet 40 to an underlying sequin sheet 40 may enable the overlying sequin sheet 40 to slide over the underlying sequin sheet 40.

For example, faces of shield sequins 44 may be smooth or coated with a nonstick or low-friction material to facilitate to movement between adjacent layered sequin sheets 40. Such materials may include, for example, polytetrafluoroethylene, polyamide-imide, nylon 6-6, nylon 4-6, graphite, graphite powder, acetal homopolymer, carbon fiber, or another friction-reducing material. Alternatively or in addition, edges of shield sequins 44 may be rounded to prevent the shield sequins 44 of adjacent layered sequin sheets 40 from catching on one another.

For example, when intended for use on a planet surface or other environment with natural or artificial gravity, a top edge of the overlying sequin sheet 40 may be sewn or otherwise attached (e.g., stapled, glued, zipped, snapped, buttoned, clipped, or otherwise attached) to the underlying sequin sheet 40. Thus, the overlying sequin sheet 40 may be draped over the underlying sequin sheet 40. Thus, a free, unattached end of the overlying sequin sheet 40 may be free to slide over the underlying sequin sheet 40, e.g., when sequined radiation protection garment 30 is arched, folded, or otherwise flexed or bent.

When intended for use under weightless conditions, more than one edge of the overlying sequined radiation protection garment 30 may be sewn or otherwise attached to the underlying sequin sheet 40. For example, in order to enable relative movement between adjacent layered sequin sheets 40, one or more edges of the overlying sequin sheet 40 may be elastically attached to the underlying sequin sheet 40. For example, an edge of the overlying sequin sheet 40 may be sewn, tethered, tied or otherwise attached to the underlying sequin sheet 40 via one or more elastic threads, bands, or other elastic connection.

Sequin sheets 40 may be layered in order to ensure that radiation protection is provided to all surface regions of a person that are covered by sequined radiation protection garment 30. For example, a shield sequin 44 of an overlying sequin sheet 40 may overlie gap 46 between adjacent shield sequins 44 of an underlying sequin sheet 40. In this manner, all gaps 46 in underlying layered sequin sheets 40 may be covered by one or more shield sequins 44 of one or more overlying sequin sheets 40.

In some cases, the number of layered sequin sheets 40 in a section of sequined radiation protection garment 30 may be determined by a degree of protection (quantified by an amount of attenuation) that is to be provided for a surface region of a person's body that the section is configured to cover. For example, a section of sequined radiation protection garment 30 that is configured to cover a body region that is more sensitive to ionizing radiation may include more layered sequin sheets 40 than a section that is configured to cover a body region that is less sensitive to the radiation.

Layered sequin sheets 40 of sequined radiation protection garment 30 may be configured to slide over one another when sequined radiation protection garment 30 is bent.

FIG. 6C schematically illustrates bending of the sequin shield element garment layer shown in FIG. 6B.

In the example shown, overlying sequin sheet 40b overlies underlying sequin sheet 40a (plus additional intervening sequin sheets 40). Sequined radiation protection garment 30 is bent such that a surface of sequined radiation protection garment 30 that is closest to overlying sequin sheet 40b is bent convexly. During the bending, overlying sequin sheet 40b may slide relative to underlying sequin sheet 40a in the direction indicated by arrow 48 (e.g., toward an edge of overlying sequin sheet 40b that is attached to underlying sequin sheet 40a). When bending in the opposite direction, the surface of sequined radiation protection garment 30 that is closest to overlying sequin sheet 40b is bent concavely. During this opposite bending, overlying sequin sheet 40b may slide relative to underlying sequin sheet 40a opposite the direction indicated by arrow 48 (e.g., in a direction away from an edge of overlying sequin sheet 40b that is attached to underlying sequin sheet 40a).

A liquid-fillable radiation protection garment 32, e.g., that is configured to be worn over sequined radiation protection garment 30 or otherwise, may be configured to enable bending of a person wearing liquid-fillable radiation protection garment 32.

Figure 7:
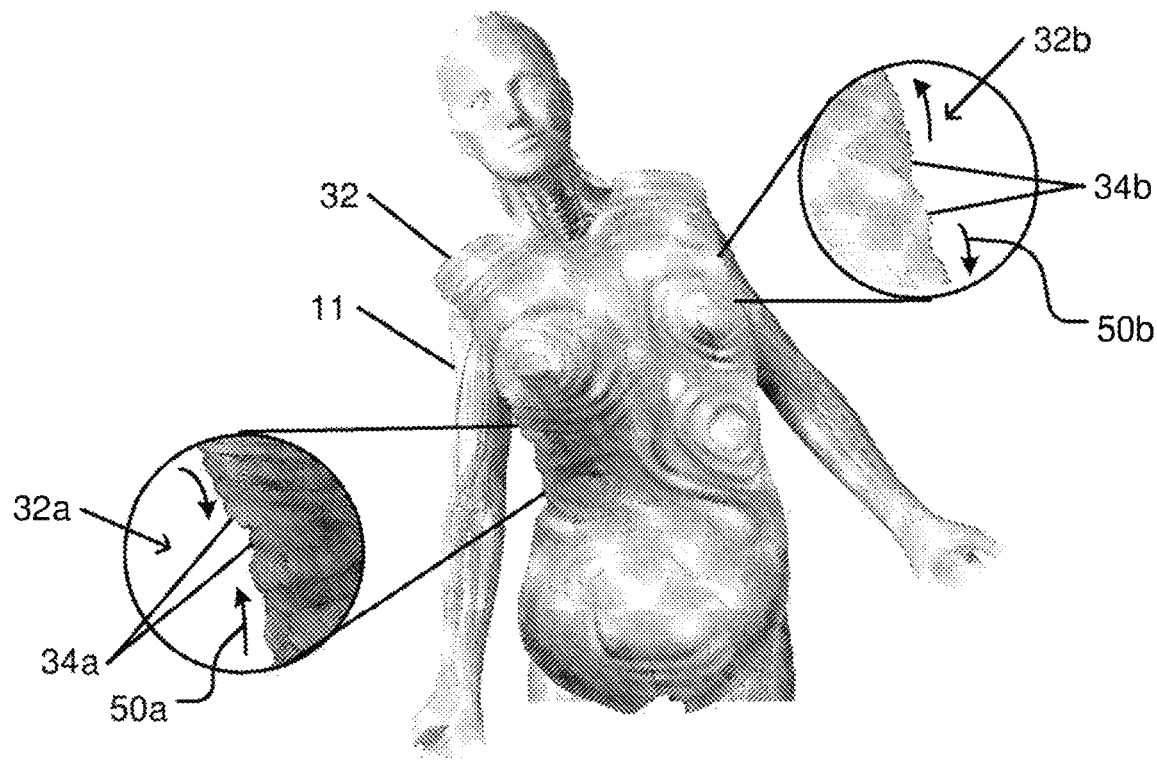
FIG. 7 schematically illustrates bending of the garment layer with liquid shield elements of a radiation protection device shown in FIG. 5C.

FIG. 7 schematically illustrates bending of the garment layer with liquid shield elements of the radiation protection device shown in FIG. 5C.

When liquid-fillable radiation protection garment 32 is bent as shown, concave liquid-fillable garment section 32a is compressed in the direction indicated by compression arrows 50a while convex liquid-fillable garment section 32b is stretched in the direction indicated by stretching arrows 50a. When concave liquid-fillable garment section 32a is compressed, bag holders 34a (each filled with a liquid bag 38) in concave liquid-fillable garment section 32a are pressed together in the direction indicated by compression arrows 50a so as to bulge outward. Similarly, when convex liquid-fillable garment section 32b is stretched, bag holders 34b in convex liquid-fillable garment section 32b are pulled away from one another in the direction indicated by stretching arrows 50b. When so pulled apart, the outer sides of bag holders 34b may be sucked inward (reducing their curvature).

A radiation protection device in accordance with an embodiment of the present invention may be provided as part of applying a method for preventing diseases that may be induced by exposure to radiation, or to which a person may be predisposed due to exposure to radiation. For example, the method may be applied to reduce the likelihood of malignancies. In particular, the method may be applied to reduce the likelihood a condition such as a cancer of the hematologic progenitor cells, leukemia, depressed immune system, or radiation sickness.

Figure 8:
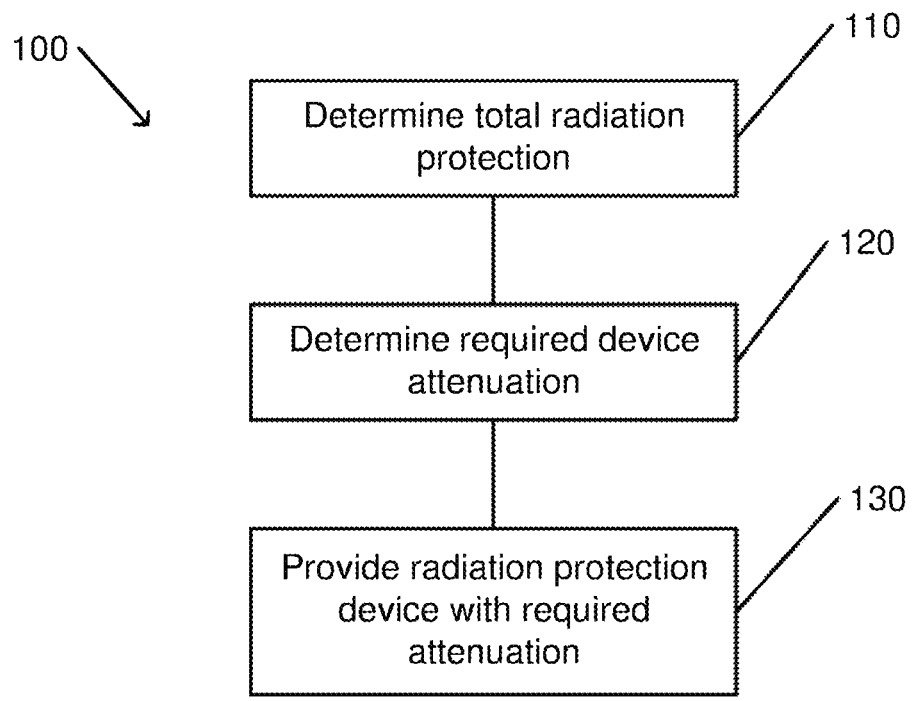
FIG. 8 is a flowchart depicting a method for preventing a radiation-related condition in a living body, in accordance with an embodiment of the present invention.

FIG. 8 is a flowchart depicting a method for preventing a radiation-related condition in a living body, in accordance with an embodiment of the present invention.

It should be understood with respect to any flowchart referenced herein that the division of the illustrated method into discrete operations represented by blocks of the flowchart has been selected for convenience and clarity only. Alternative division of the illustrated method into discrete operations is possible with equivalent results. Such alternative division of the illustrated method into discrete operations should be understood as representing other embodiments of the illustrated method.

Similarly, it should be understood that, unless indicated otherwise, the illustrated order of execution of the operations represented by blocks of any flowchart referenced herein has been selected for convenience and clarity only.

Operations of the illustrated method may be executed in an alternative order, or concurrently, with equivalent results. Such reordering of operations of the illustrated method should be understood as representing other embodiments of the illustrated method.

Operations of radiation protection method 100 may be executed by a person who is designing or assembling a radiation protection device, in accordance with an embodiment of the present invention. For example, the radiation protection device may be designed for a particular person for use under one or more predetermined conditions. Radiation protection requirements for a person (e.g., a maximum allowable radiation dose or exposure) may be determined by one or more characteristics of the person to be protected. The predetermined conditions may be related to anticipated locations of the person and anticipated activities of the person at the anticipated locations.

A required total attenuation ($A_R$) may be determined (block 110).

The required total attenuation may vary according to the use for which the radiation protection device is intended. For example, when intended for continued use involving lengthy exposure to radiation, $A_R$ may be relatively high. Such a configuration may be applicable to first responders who remain in disaster zones and to interplanetary space travel. When intended for short term use, $A_R$ may be relatively low. Such a configuration may be applicable to individuals being evacuated from disaster zones.

The determination of $A_R$ may be such that a radiation-induced condition is prevented under an anticipated exposure of the person to radiation.

For example, the determination of $A_R$ may be such that the surviving volume of active bone marrow is sufficient to allow for hematopoietic reconstitution after exposure. For example, this volume may range between 23 cm³ and 58 cm³ of active marrow, depending on the size of the individual. In some cases, $A_R$ may be calculated by $$A_R \geq \frac{D_u}{D_v},$$

where $D_U$ is the unprotected radiation dose and $D_v$ is the dose at which the required percent viability of bone marrow is the required volume for hematopoietic reconstitution.

For example, if the intended use requires exposure to 1000 rad/hour for one hour ($D_U$=1000 rad), and the radiation protection device protects in a substantially uniform manner 150 cm³ of active bone marrow, and 41 cm³ of bone marrow is required to survive, then the level of protection is required to be 27%. A maximum allowable dose for 27% survival of bone marrow cells may be 200 rad ($D_v$). Thus, $A_R$ for this case is 5.

A required attenuation by the radiation protection device ($A_D$) may be calculated (block 120).

For example, various imaging technologies (e.g., computed tomography, magnetic resonance imaging, or other imaging) may be used to determine the nature of tissue that surrounds an interior region of the body that is to be protected. For example, the analysis may be particular to a particular person, or may be based on a population of similar people. Based on the characteristics (e.g., composition and dimensions) of surrounding tissue, tissue attenuation $A_T$ may be determined. The attenuation $A_D$ may then be determined from $A_R$ and $A_T$ (for a point at coordinates x, y, z) by $$A_D(x, y, z) = \frac{A_R}{A_T}.$$

In the above example, where $A_R$ is calculated to be 5 and if $A_T$ is determined to be 2, $A_D$ may be required to be 2.5.

Figure 9A:
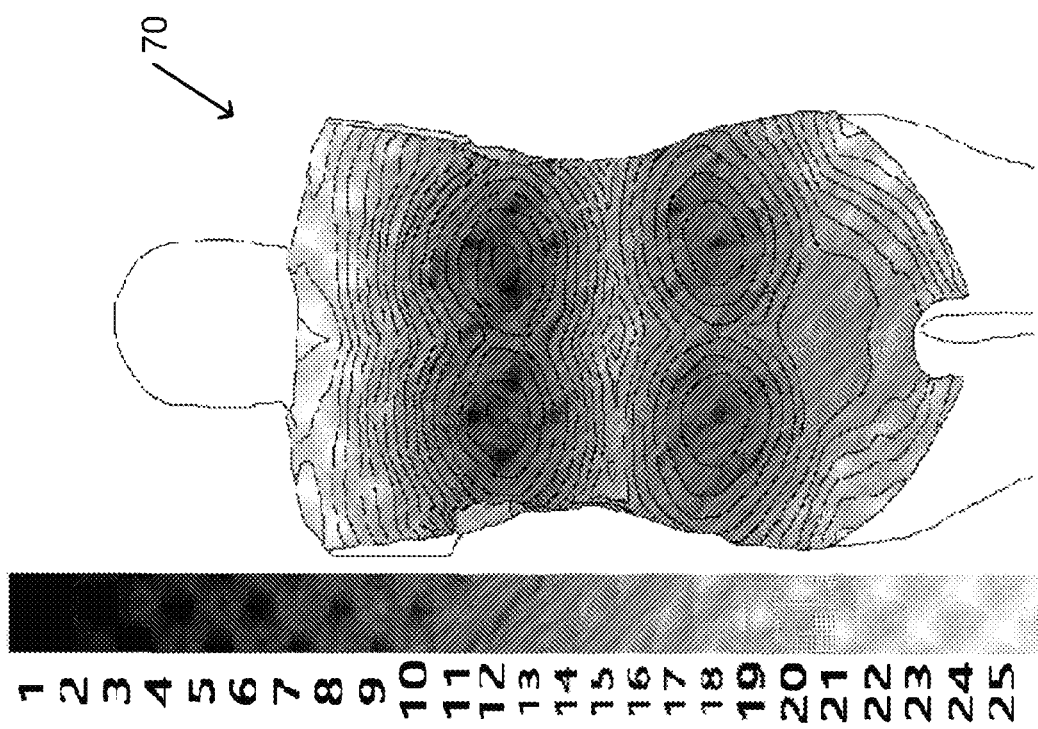
FIG. 9A schematically illustrates a front part of a map of self-shielding by body tissue for radiation-sensitive internal regions in a person, for use in design of a radiation protection device in accordance with an embodiment of the present invention.
Figure 9B:
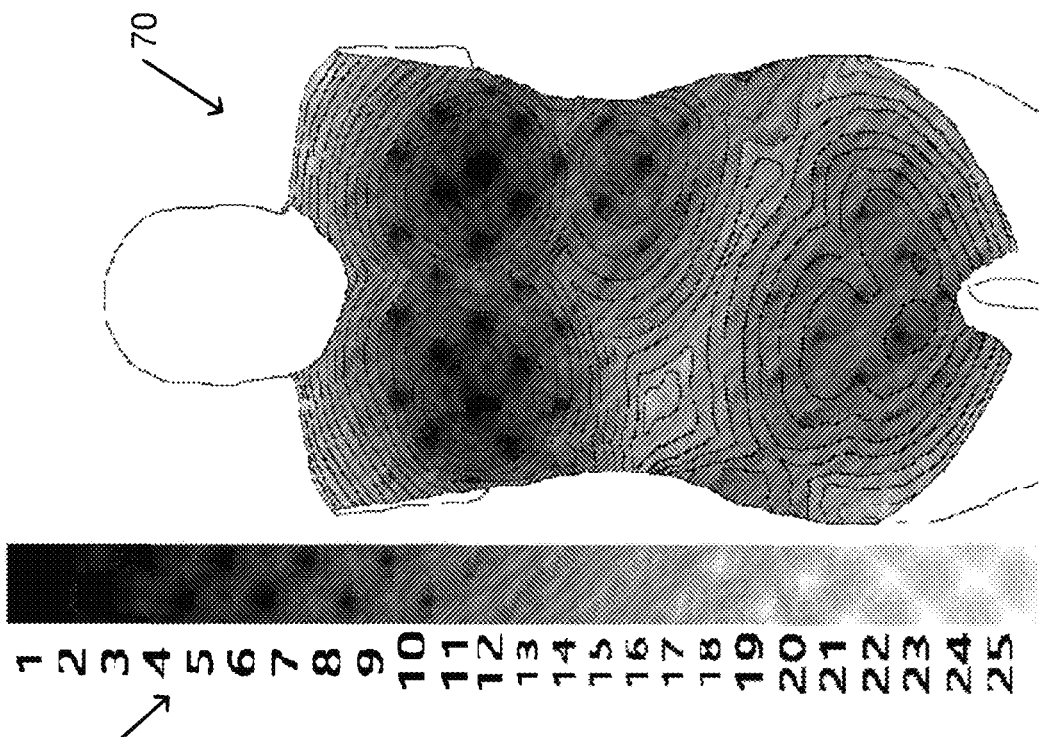
FIG. 9B schematically illustrates a rear part of the self-shielding map shown in FIG. 9A.

FIG. 9A schematically illustrates a front part of a map of self shielding by body tissue of radiation sensitive interior regions in a person, for use in design of a radiation protection device in accordance with an embodiment of the present invention. FIG. 9B schematically illustrates a rear part of the self-shielding map shown in FIG. 9A.

Self-shielding map 70 indicates the areal density of shielding (e.g., in units of g/cm2 as indicated by legend 72) that is provided by body tissue of a person to one or more radiation sensitive interior regions within the person's body. In the example, shown, the radiation sensitive interior regions include the ovaries, stomach, colon, glandular breast tissue, hematopoietic stem cells of the iliac crest, and tissue resident stem cells in the distal airways of the lungs.

For example, self-shielding densities of self-shielding map 70 may be calculated on the basis of one or more of measurements on human bodies, measurements on phantoms, measurements on animals, simulations, calculations based on a model, or another technique for determining self-shielding by human tissue. Other quantities may be used to indicate self-shielding by human tissue (e.g., transmission, attenuation, or another quantity indicative of self-shielding by tissue).

For example, self-shielding to the radiation-sensitive interior regions may be determined by tracing rays that originate from the radiation-sensitive interior regions to the surface of the body. The local distance and density of the tissue (e.g., bone, muscle, adipose, or other tissue) that is traversed by each ray may be multiplied and integrated along the path of the ray.

A radiation protection device is provided that provides the calculated device attenuation (block 130).

In some cases, the required thickness of shielding (e.g., number or size of shield elements) that cover that interior region may be calculated as ln ($A_D$)/μ, where μ is the linear attenuation coefficient (e.g., in units of cm$^{-1}$). In some cases, e.g., where radiation scattering significantly contributes to the attenuated radiation, other factors (e.g., a buildup factor or other factor) may be taken into account when calculating the required thickness.

Figure 10A:
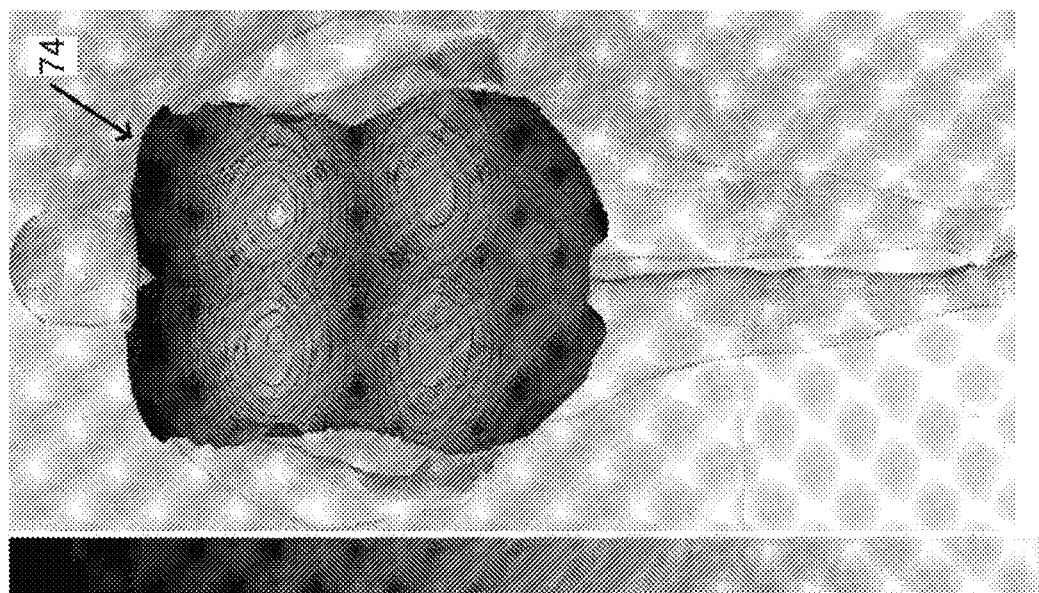
FIG. 10A schematically illustrates a map of a distribution of radiation shielding on a front of a radiation protection device that is designed in consideration of the self-shielding map shown in FIG. 9A.
Figure 10B:
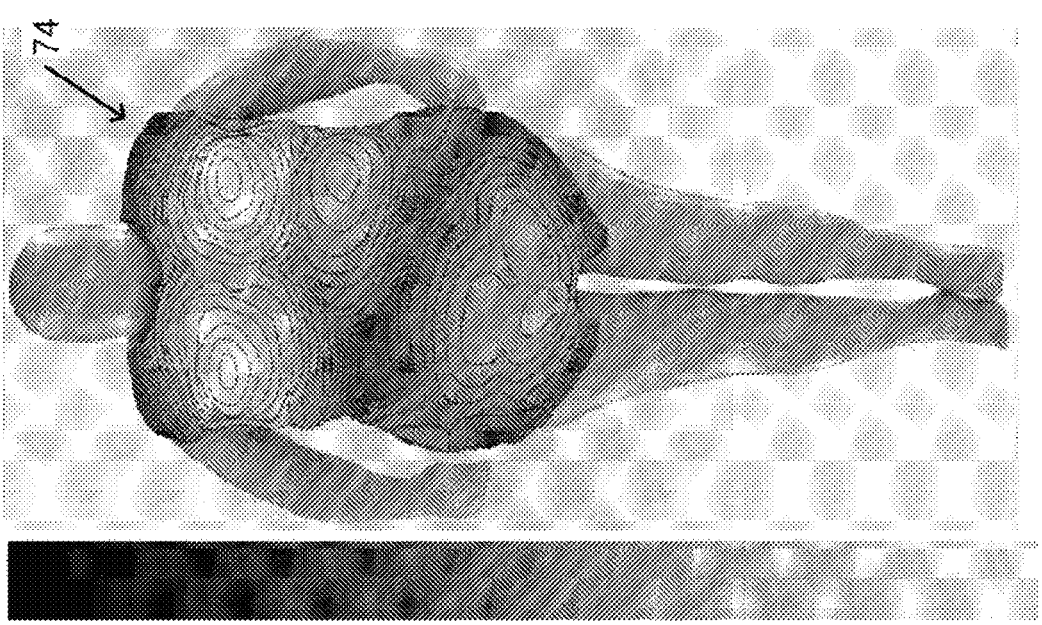
FIG. 10B schematically illustrates a map of a distribution of radiation shielding on a rear of a radiation protection device that is designed in consideration of the self-shielding map shown in FIG. 9B.

FIG. 10A schematically illustrates a map of a distribution of radiation shielding on a front of a radiation protection device that is designed in consideration of the self-shielding map shown in FIG. 9A. FIG. 10B schematically illustrates a map of a distribution of radiation shielding on a rear of a radiation protection device that is designed in consideration of the self-shielding map shown in FIG. 9B.

Device shielding map 74 indicates the areal density of shielding (e.g., in units of g/cm2 as indicated by legend 72) that is provided by a radiation protection device when worn by a person. For example, shielding densities of device shielding map 74 may be calculated on the basis of one or more of a design of the radiation protection device, measurements (e.g., of radiation transmission) of a radiation protection device, or another technique for determining shielding by a radiation protection device. Other quantities may be used to indicate shielding by a radiation protection device (e.g., transmission, attenuation, or another quantity indicative of shielding by the radiation protection device).

A radiation protection device whose shielding is as indicated by device shielding map 74 may be worn on by a person whose self-shielding is as indicated by self-shielding map 70. In this case, the total shielding of sensitive interior region of the person may be found by combining the shielding that is indicated by the combination of device shielding map 74 and self-shielding map 70 (e.g., additively combining when areal density is mapped, multiplicatively when attenuation is mapped, or using another appropriate the combination technique).

The total required radiation attenuation in areal density in order to achieve a desired absorbed dose reduction for a given material may be determined based on theoretical or experimentally determined values for a given spectrum of a mixed field of radiation. In order to provide a given amount of desired attenuation (e.g., equivalent to 26 $g/cm^2$ areal density) to each radiation-sensitive interior region of the body, the thickness (e.g., areal density) of each shielding element may be selected to augment self-shielding of the radiation-sensitive interior region by the body such that for each point on the surface the areal density provided to each protected tissue/organ is at least 26 $g/cm^{\wedge}2$ by adding the areal density of self shielding plus the areal density of the shielding elements at each point. For example, if at a particular point on the surface of the body there is 20 $g/cm^2$ of self-shielding by tissue between that point and the radiation-sensitive interior region, and if the density of the shielding elements that cover that point is 1 $g/cm^3$, then the shielding elements at this point may be 6 cm thick with an areal density of 6 $g/cm^2$. Therefore, the thickness of the shielding over the surface may vary widely based on the self-shielding at various points and depending on the density of the shielding elements that cover each point.

A material may be selected in accordance with a type of radiation to which a person is expected to be exposed. For example, the most effective material per unit mass of shield for radiation in space (e.g., primarily energetic protons and other small nuclei from solar particle events and galactic cosmic radiation) may be provided by hydrogen. Shields of heavier elements, lead for example, while commonly used for x- or γ-ray absorption, may be less efficient per unit mass than lighter elements for absorbing energetic nuclear particles (and may contribute to the radiation by producing short-range heavy nuclear fragments and penetrating neutrons).

The radiation protection device may be worn by an astronaut or another user in order to maximize the shielding thickness across the solid angle covered. A radiation protection device may be designed so as to enable movement by a person wearing the device. For example, under weightless conditions, a physical thickness of the radiation protection device, rather than the total mass may be made sufficiently small so as not to limit mobility. For example, use of graded shield elements consisting of successive layers of high density, high atomic number materials, and low density, hydrogen-rich compounds may be utilized to reduce thickness (as is sometimes used for radiation hardening of active electronic components).

Radiation shielding elements of the radiation protection device may be arranged in layers, or as separate layered garments. Such layering may enable mobility of a user of the device. Furthermore, when worn as separate layered garments, different combinations of garments may be utilized under different circumstances. For example, garments to be worn may be selected in accordance with a planned activity and an anticipated exposure to radiation during that activity.

Protection of various interior regions of a body of a person may be designed, or a design evaluated, using ray-tracing techniques or other techniques for calculating exposure to radiation.

For example, in order to determine the ability of the radiation protection device to protect a user wearing the device, radioisotope sources, particle (e.g., proton) accelerators (e.g., designed to mimic space radiation), or other sources may be placed in a uniform pattern around an anatomically accurate human phantom. Radiation doses received at these concentrations in the presence and absence of the radiation protection device may be measured. For example, an accurate phantom may include a human skeleton with thermoluminescent dosimeters embedded in bone marrow centers and surrounded by water to simulate human tissue. The dose with and without the radiation protection device may be compared.

For example, foci of protection may be designated within the body. The body may be a standard body (e.g., based on a collection of internal measurements or images, such as is available via the Visible Human Project), or may be based on interior imaging (e.g., computed tomography or magnetic resonance imaging scans) of a particular body. The foci of protection may be defined as three-dimensional coordinates of the center of masses of stem cell niches that are to be protected by the radiation protection device. Such niches may include, for example, areas within the lungs, iliac red bone marrow, and ovaries which had the highest concentrations of stem cells. For organs with bilateral stem cell niches (e.g., lungs, iliac red bone marrow, and ovaries), two foci of protection may be designated; one for each side.

For some radiation types, such as those encountered in space where the energy spectrum is highly variable and the radiation field is mixed (different types of radiation may be incident simultaneously), radiation protection method 100 may be modified.

The propagation of some radiation types, such as protons and alpha radiation, is characterized by a Bragg peak. The Bragg peak corresponds to path length at which there is a sharp increase in energy deposition before the end of its track length. In this case, the required total attenuation may be selected to ensure that the Bragg peak does not occur within a radiation-sensitive interior region. For example, if a spectrum of protons has a maximum energy of 100 MeV with a Bragg peak ending at 77 $g/cm^2$ in liquid water (which has comparable stopping power to human body tissue), then the required total attenuation may be determined to be at least 77 $g/cm^2$. If, at a particular point on the surface of the body, the self-shielding of tissue that lies between the skin surface and a radiation-sensitive interior region is 55 $g/cm^2$, then the radiation protection device should provide 22 $g/cm^2$ of shielding at that point. If the shielding elements are composed of liquid water with a density of 1 $g/cm^3$, then the shielding thickness at that point would be 22 cm.

The areal density values for required total attenuation, self-shielding attenuation, and shielding element attenuation may be adjusted based on the total stopping power for a specific composition of a shielding material and a type of incident radiation.

The shielding elements used to shield one interior region of the body may be different from those used to shield another interior region. For example, ergonomic constraints (allowing range of motion and flexibility) may determine that denser (e.g., than water) materials should be used to shield some areas of the body in order to reduce the required thickness. Similarly, ergonomic constraints may determine the flexibility of different sections of the radiation protection device that are configured to shield different interior regions of the body.

Different embodiments are disclosed herein. Features of certain embodiments may be combined with features of other embodiments; thus certain embodiments may be combinations of features of multiple embodiments. The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A device for protection of a body from radiation, the device comprising:
    at least one flexible garment, each section of said at least one flexible garment being configured to shield a region of a surface of the body; and
    a plurality of shield elements incorporated into a flexible substrate of the at least one flexible garment, comprising:
        a plurality of liquid bags, each of the bags being configured to be filled with a liquid and cover the region of the surface of the body.

2. The device of claim 1, wherein the flexible substrate comprises a plurality of flexible bag holders, each of said plurality of bags being configured to be inserted into a bag holder of said plurality of flexible bag holders.

3. The device of claim 1, wherein a shield element of said plurality of shield elements comprises a plurality of stacked liquid-fillable compartments.

4. The device of claim 1, further comprising a tube to enable introduction of a liquid into a liquid-fillable compartment of said plurality of stacked liquid fillable compartments or removal of the liquid from the liquid-fillable compartment of said plurality of stacked liquid-fillable compartments.

5. The device of claim 1, wherein said plurality of shield elements is embedded within the flexible substrate.

6. The device of claim 1, wherein each of said plurality of shield elements has an inward facing surface that is greater than an opposite outward facing surface, such that tapering gaps are formed in between adjacent shield elements of said plurality of shield elements.

7. The device of claim 6, wherein the substrate fully or partially fills the gaps.

8. The device of claim 1, wherein said plurality of shield elements comprises a plurality of sequins that are attached to the flexible substrate and wherein the flexible surface comprises a fabric sheet.

9. The device of claim 8, wherein the fabric sheet forms a webbing between said plurality of sequins.

10. The device of claim 8, wherein a garment of said at least one garment comprises a plurality of the fabric sheets formed into layers.

11. The device of claim 10, wherein a sequin of said plurality of sequins on one fabric sheet of said plurality of the fabric sheets is positioned to overlie a gap between adjacent sequins of said plurality of sequins on another fabric sheet of said plurality of fabric sheets.

12. The device of claim 1, wherein said at least one garment comprises a plurality of garments that are configured to be worn in layers,
    wherein one garment of said plurality of garments is configured such that a shield element of said plurality of shield elements on said one garment is configured to overlie a gap between two adjacent shield elements on another garment of said plurality of garments.

13. A method for preventing a radiation-induced condition in a body in space, the method comprising:
    determining a required attenuation of radiation at an interior region of the body so as to prevent the radiation-induced condition under an anticipated exposure of the body to radiation;
    providing a radiation protection device comprising at least one flexible garment, each section of said at least one flexible garment; and
    providing a plurality of shield elements incorporated into a flexible substrate of the at least one flexible garment and having a plurality of bags, each of the bags being configured to be filled with a liquid and a volume of liquid configured to attenuate the determined radiation.

14. The method of claim 13, wherein determining the required radiation attenuation comprises determining an attenuation required to prevent a Bragg peak of the radiation from occurring within the interior region.

15. The method of claim 13, wherein determining the required attenuation of radiation comprises:
    determining total areal density of shielding to the interior region to prevent the radiation-induced condition, and
    determining the volume of each of the plurality of bags for each interior region.

16. The method of claim 13, wherein the plurality of bags comprise a plurality of stacked liquid-fillable compartments.

* * * * *